United States Patent [19]

Moyer et al.

[11] Patent Number: 5,506,235
[45] Date of Patent: Apr. 9, 1996

[54] QUINOLINE DERIVATIVES AS IMMUNOSTIMULANTS

[75] Inventors: Mikel P. Moyer, Clinton; James W. McFarland, Lyme, both of Conn.

[73] Assignee: Pfizer Inc., New York, N.Y.

[21] Appl. No.: 190,113

[22] PCT Filed: Jul. 1, 1992

[86] PCT No.: PCT/US92/05435

§ 371 Date: Jan. 2, 1994

§ 102(e) Date: Jan. 2, 1994

[87] PCT Pub. No.: WO93/03030

PCT Pub. Date: Feb. 18, 1993

Related U.S. Application Data

[63] Continuation of Ser. No. 740,825, Aug. 2, 1991, abandoned.

[51] Int. Cl.[6] .......... A61K 31/44; A61K 31/535; C07D 471/04; C07D 413/14
[52] U.S. Cl. .......... 514/293; 514/232.8; 544/126; 546/82
[58] Field of Search .......... 514/232.8, 293; 544/126; 546/82

[56] References Cited

U.S. PATENT DOCUMENTS

| | | | |
|---|---|---|---|
| 3,859,291 | 1/1975 | Burch | 260/286 |
| 3,919,238 | 11/1981 | Spencer et al. | 260/288 |
| 4,716,168 | 12/1987 | Alaimo | 514/293 |
| 5,145,843 | 9/1992 | Arnold | 514/63 |

FOREIGN PATENT DOCUMENTS

| | | |
|---|---|---|
| 0187705 | 7/1986 | European Pat. Off. . |
| 5389 | 9/1967 | France . |
| 2047882 | 3/1971 | France . |
| 2321291 | 3/1977 | France . |
| 980394 | 3/1965 | United Kingdom . |

OTHER PUBLICATIONS

Alaimo et al., *Imidazo[4,5-f]quinolines, 4, Synthesis and Anthelmintic Activity of a Series of Imidazo[4,5-f]quinolin-9-ols*, 21, 3, Journal of Medicinal Chemistry, 298–300 (1978).

Spencer et al., *Imidazo[4,5-f]quinolines. 2. A series of 9-(Substituted amino)imidazo]4,5-f]quinolines as Antitapeworm Agents*, 20, 6, Journal of Medicinal Chemistry, 829–833 (1977).

A Desvignes et al., *Recherche sur les aminoquinoleines. XVIII. Activite antibacterienne et antifongique in vitro d'alkylamino–4 quinoleines a longues chaines*, 35, 7–8, Annales Pharmaceutiques Francaises, 239–247 (1977).

S. Renault et al., *Recherche sur les aminoquinoleines. XIV: alkylamino–4 quinoleines a longues chaines a activite amoebicide potentielle*, 11, 6, European Journal of Medicinal chemistry, 547–554 (1976).

S. Renault et al., *Recherche sur les aminoquinoleines, XV: alkylamino–4 quinoleines et quinaldines a longues chaines a activite amoebicide potentielle*, 11, 6, European Journal of Medicinal Chemistry, 555–560, (1976).

S. Renault et al., *Recherche sur les aminoquinoleines. XVI: Alkylamino–4 quinoleines et quinaldines a longues chaines a activite amoebicide potentielle*, 11, 6, European Journal of Medicinal Chemistry, 561–565 (1976).

A. Allais et al., *Recherche de composés analgésiques non narcotiques. Étude de novelles (alcoxycarbonyl–2'phénylamino)–4 quinoléines et de molécules apparentées*, 2, Chimie Therapeutic, 154–168 (1973).

Primary Examiner—Marianne M. Cintins
Assistant Examiner—Phyllis G. Spivack
Attorney, Agent, or Firm—Peter C. Richardson; Paul H. Ginsburg; Garth Butterfield

[57] ABSTRACT

This invention relates to compounds of the formula

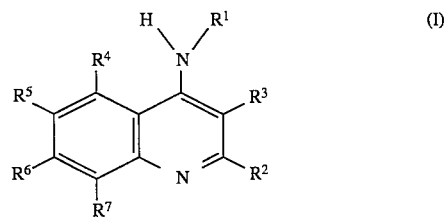

wherein $R^1$, $R^2$, $R^3$, $R^4$, $R^5$, $R^6$ and $R^7$ are as defined hereinbelow that exhibit activity as immunostimulants.

6 Claims, No Drawings

QUINOLINE DERIVATIVES AS IMMUNOSTIMULANTS

This case is a continuation of PCT/US92/05435, which is a continuation of U.S. Ser. No. 07/740,825, filed Aug. 2, 1991, now abandoned.

The present invention relates to novel quinoline derivatives that exhibit activity as immunostimulants. By improving a host's immune response, the compounds of this invention increase the host's resistance to infection or infestation by bacteria, viruses, fungi, etc. They are therefore useful, alone or in combination with anti-infective therapy, in the prophylactic or therapeutic treatment of any infectious disease.

U.S. Pat. No. 4,716,168, assigned to Norwich Eaton Pharmaceuticals, Inc. refers to other quinoline derivatives, more specifically, to imidazo(4,5-f)quinolines, and states that such compounds are useful in enhancing the immune response system of a mammal.

SUMMARY OF THE INVENTION

The present invention relates to compounds of the formula

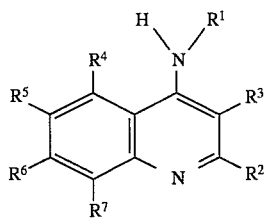

(I)

wherein $R^1$ is $(C_3-C_{18})$ alkyl or phenyl optionally substituted with from one to three substituents independently selected from $(C_1-C_6)$ alkyl, $(C_1-C_6)$ alkoxy, halo, cyano, $(C_3-C_8)$ cycloalkyl-$(C_1-C_6)$alkoxy wherein the cycloalkyl moiety may be substituted with from one to three $(C_1-C_6)$alkyl groups; hydroxyl, benzyloxy, carboxyl, hydroxy-$(C_1-C_6)$ alkyl, pyrrolidino, piperidino, morpholino and —CONHQCOOH wherein Q is $(C_1-C_4)$ alkyl;

$R^2$ is hydrogen, $(C_1-C_6)$ alkyl, $(C_3-C_7)$ cycloalkyl, phenyl or phenyl-$(C_1-C_6)$ alkyl, wherein the phenyl moieties of said phenyl and said phenyl-(C1-$C_6$) alkyl may be optionally substituted with from one to three substituents independently selected from $(C_1-C_6)$ alkyl, $(C_1-C_6)$-alkoxy, halo, cyano and benzyloxy;

each of $R^3$ and $R^4$ is hydrogen;

$R^5$ is hydrogen, amino, hydroxyl, 5-pyrazolyl, guanidino, hydroxy-$(C_1-C_6)$ alkyl, —NHC(=$NR^8$)$R^9$, —NHSO$_2R^{11}$, —NHCOR$^{12}$ or ureido;

or $R^4$ and $R^5$, together with the carbons to which they are attached, form a group of the formula

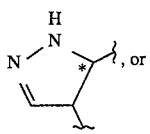, or

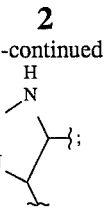

wherein the carbon of group A labelled with an asterisk (*) represents the point of attachment of $R^4$ to the quinoline nucleus and the carbon of group A adjacent to it represents the point of attachment of $R^5$ to the quinoline nucleus;

$R^6$ is hydrogen hydroxyl, amino guanidino —NHC(=$NR^8$)$R^9$, —NHCOR$^{13}$, —NHSO$_2R^{13}$, or ureido;

$R^7$ is hydrogen, halo, hydroxyl, amino, —NHC(=$NR^8$)$R^9$, —NHSO$_2R^{14}$, —NHCOR$^{14}$, ureido or guanidino;

$R^8$ and $R^9$ are independently selected from hydrogen, phenyl and $(C_1-C_6)$alkyl;

$R^{11}$, $R^{12}$, $R^{13}$ and $R^{14}$ are independently selected from $(C_1-C_6)$ alkyl and phenyl optionally substituted with halo, $(C_1-C_6)$alkyl or $(C_1-C_6)$alkoxy;

except for 6-amino-4-anilino-2-phenylquinoline hydrochloride, 6-amino-4-(m-anisidino)-2-phenylquinoline hydrochloride, 6-amino-4-cyclohexylamino-2-phenylquinoline hydrochloride, 6-amino-4-(m-anisidino)-2-methylquinoline methanesulfonate, 6-amino-4-(p-toluidino)-2-methylquinoline methanesulfonate, 9-(p-anisidino)-2-methyl-1H-pyrazolo[3,4 -f]quinoline hydrochloride, 9-(cyclohexylamino)-1H-pyrazolo[ 3,4-f]quinoline methanesulfonate, 9-(cyclopentylamino)-1H-pyrazolo[3,4-f]quinoline methanesulfonate, 4-(phenylamino)-2-phenylquinolin-6-ol hydrobromide; 4-(butylamino)-2-phenylquinolin-6-ol hydrobromide; 4-[(3-methoxyphenyl)amino]-2 -methylquinolin-7-ol hydrochloride; 4-[(4-chlorophenyl)amino]-2 -methylquinolin-7-ol hydrobromide; 4-(cyclohexylamino)-2 -methylquinolin-6-ol hydrochloride; 4-[(3-methoxyphenyl)amino] quinolin-6,8-diol hydrochloride; and 4-(cyclohexylamino)quinolin- 8-ol hydrochloride.

This invention also relates to the pharmaceutically acceptable acid addition salts and cationic salts of compounds of the formula I.

Unless otherwise indicated, the term "halo" as used herein, includes fluoro, chloro, bromo and iodo.

Unless otherwise indicated, the term "alkyl" as used herein, may be straight, branched or cyclic, and may include straight and cyclic moieties as well as branched and cyclic moieties.

The compounds of formula I may have chiral centers and therefore may occur in different stereoisomeric configurations. The invention includes all stereoisomers of such compounds of formula I, including mixtures thereof.

The present invention also relates to all radio-labelled forms of the compounds of the formula I. Such radio-labelled compounds are useful as research and diagnostic tools in metabolism pharmacokinetic studies and in binding assays in both animals and man.

The present invention also relates to a pharmaceutical composition for enhancing or stimulating the immune response of vertebrates, including humans, cattle, swine and poultry, comprising an immune response enhancing or stimulating amount of a compound of the formula I, or a pharmaceutically acceptable salt thereof, and a pharmaceutically acceptable carrier.

The present invention also relates to a method for enhancing or stimulating the immune response of vertebrates, including humans, cattle, swine and poultry, comprising administering to a vertebrate an immune response enhancing or stimulating amount of a compound of the formula I, or a pharmaceutically acceptable salt thereof.

Preferred compounds of this invention are compounds of the formula I wherein $R^3$, $R^6$ and $R^7$ are hydrogen, and $R^4$ and $R^5$, together with the carbons to which they are attached, form a group of the formula

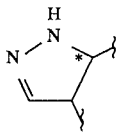

A wherein the carbon labelled with an asterisk (*) represents the point of attachment of $R^4$ to the quinoline nucleus and the adjacent carbon of group A represents the point of attachment of $R^5$ to the quinoline nucleus.

Other preferred compounds of this invention are compounds of the formula I wherein $R^3$, $R^4$, $R^6$ and $R^7$ are hydrogen and $R^5$ is amino, $-NHSO_2R^{11}$, $-NHCOR^{12}$ or hydroxy Specific preferred compounds of this invention are:
9-(m-Anisidino)-7-methyl-1H-pyrazolo[3,4-f]quinoline hydrochloride;
9-(p-Cyclohexylmethoxyanilino)-7-methyl-1H-pyrazolo[3,4-f]quinoline;
9-(Cyclohexylamino)-7-methyl-1H-pyrazolo[3,4-f] quinoline;
9-(p-Cyclohexylmethoxyanilino)-1H-pyrazolo[3,4-f] quinoline;
6-Amino-4-(p-cyclohexylmethoxyanilino)-2-phenylquinoline;
6-Amino-4-(p-chloroanilino)-2-phenylquinoline;
4-(p-Cyclohexylmethoxyanilino)-6-methylsulfonamido-2-phenylquinoline;
4-Decylamino-2-methylquinolin-6-ol;
4-Tetradecyl-2-methylquinolin-6-ol;
4-(Dodecylamino)quinolin-6-ol;
Other compounds of the invention are:
9-(p-Butoxyanilino)-7-methyl-1H-pyrazolo[3,4-f] quinoline;
9-(p-Chloroanilino)-7-methyl-1H-pyrazolo[3,4-f] quinoline;
9-(p-Benzyloxyanilino)-7-methyl-1H-pyrazolo[3,4-f] quinoline;
9-(p-Hydroxyanilino)-7-methyl-1H-pyrazolo[3,4-f] quinoline;
9-(m-Anisidino)-7-methyl-1H-triazolo[3,4-f]quinoline;
9-(m-Anisidino)-1H-pyrazolo[3,4-f]quinoline;
9-(p-Chloroanilino)-1H-pyrazolo[3,4-f]quinoline;
6-Amino-4-(p-butoxyanilino)-2-phenylquinoline;
6-Amino-4-(p-anisidino)-2-phenylquinoline;
4-(m-Anisidino)-2,methyl-6-(5-pyrazolo)quinoline;
4-(p-Cyclohexylmethoxyanilino)-2-methyl-6-(5-pyrazolo)quinoline;
9-(4-Ethylanilino)-7-methyl-1H-pyrazolo[3,4-f] quinoline;
7-Methyl-9-(4-propylanilino)-1H-pyrazolo[3,4-f] quinoline;
7-Methyl-9-(4-toluidino)-1H-pyrazolo[3,4-f]quinoline;
9-Cyclopentylamino-7-methyl-1H-pyrazolo[3,4-f] quinoline;
9-(4-Ethoxyanilino)-1H-pyrazolo[3,4-f]quinoline;
9-(4-Ethylanilino)-1H-pyrazolo[3,4-f]quinoline;
9-(4-Propylamino)-1H-pyrazolo[3,4-f]quinoline;
9-(4-Butylanilino)-1H-pyrazolo[3,4-f]quinoline;
9-(p-Toluidino)-1H-pyrazolo[3,4-f]quinoline;
9-(4-Butoxyanilino)-1H-pyrazolo[3,4-f]quinoline;
6-Amino-4-(m-anisidino)quinoline;
6-Amino-4-(p-butoxyanilino)quinoline;
6-Amino-4-(3,4-difluoroanilino)-2-phenylquinoline; 4-(p-Cyclohexylmethoxyanilino)-2-phenyl-6-ureidoquinoline;
6-Acetamido-4-(p-cyclohexylmethoxyanilino)-2-phenylquinoline;
N-[4-(Cyclohexylmethyloxy)phenyl]-2-methylquinolin-4, 8-diamine;
4-(4-Butylphenylamino)-2-methylquinolin-6-ol;
4-(4-Chlorophenylamino)-2-methylquinolin-6-ol;
4-(4-Chlorophenylamino)-2-phenylquinolin-6-ol;
2-Methyl-4-octylaminoquinolin-6-ol Hydrobromide;
4-[4-(Cyclohexylmethyloxy)phenylamino]-2-methylquinolin- 6-ol;
4-(3-Methoxyphenylamino)-2-methylquinolin-6-ol;
4-Hexylamino-2-methylquinolin-6-ol;
4-Dodecylamino-2-methylquinolin-6-ol;
4-[(3-Methoxyphenyl)amino]quinolin-6-ol; 4-[(4-Cyclohexylmethyloxy)phenylamino]quinolin-6-ol;
4-(Cyclohexylamino)quinolin-6-ol;
4-(Decylamino)quinolin-6-ol;
4-(4-Butylphenylamino)-2-methylquinolin-7-ol;
4-[4-(Cyclohexylmethyloxy)phenylamino]-2-methylquinolin- 7-ol;
4-(Dodecylamino)-2-methylquinolin-7-ol;
4-(Decylamino)-2-methylquinolin-7-ol;
4-(4-Butylphenylamino) quinolin-8-ol;
4-[4-(Cyclohexylmethyloxy)phenylamino]quinolin-8-ol;
4-(Dodecylamino)quinolin-8-ol;
4-[4-(Cyclohexylmethyloxy)phenylamino]quinolin-6,8diol; and
4-[4-(Cyclohexylmethyloxy)phenylamino]quinolin-6-methanol.

Examples of other compounds of the formula I include:
7-methyl-9-(4-pyrrolidinoanilino)-1H-pyrazolo[3,4-f] quinoline hydrochloride;
9-(4-aminohippuroyl)-7-methyl-1H-pyrazolo[3,4-f]quinoline hydrochloride;
9-(4-carboxyanilino)-7-methyl-1H-pyrazolo[3,4-f]quinoline hydrochloride;
9-(m-anisidino)-7-cyclohexyl-1H-pyrazolo[3,4-f] quinoline hydrochloride;
4-(m-anisidino)-6-phenylsulfonamidoquinoline hydrochloride;
4-(m-anisidino)-7-methylsulfonamidoquinoline hydrochloride;
4-(m-anisidino)-8-methylsulfonamidoquinoline hydrochloride;
4-(p-ethoxyanilino)-6-guanidinoquinoline hydrochloride;
4-(p-cyclohexylmethoxyanilino)-6-guanidinoquinoline hydrochloride;
4-(p-ethoxyanilino)-7-guanidinoquinoline hydrochloride;
4-(p-cyclohexylmethoxyanilino)-7-quanidinoquinoline hydrochloride;
4-(p-ethoxyanilino)-8-guanidinoquinoline hydrochloride;
4-(p-cyclohexylmethoxyanilino)-8-guanidinoquinoline hydrochloride;
6-acetamidino-4-(m-anisidino)quinoline hydrochloride;
7-acetamidino-4-(m-anisidino)quinoline hydrochloride;
8-acetamidino-4-(m-anisidino)quinoline hydrochloride;
7-amino-4-(m-anisidino)quinoline hydrochloride;
4-(p-cyclohexylmethoxyanilino)-7-ureidoquinoline hydrochloride;
4-(p-cyclohexylmethoxyanilino)-8-ureidoquinoline hydrochloride;

DETAILED DESCRIPTION OF THE INVENTION

The reaction scheme below illustrates the synthesis of the compounds of this invention. In the reaction schemes and discussion that follow, except where otherwise stated, formula I and substituents R¹ through R¹⁴ are defined as above.

SCHEME

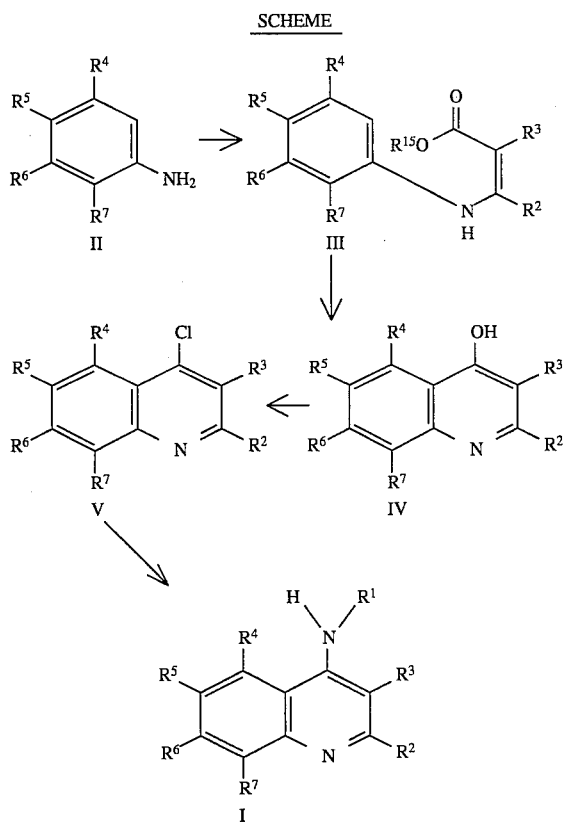

The above reaction scheme illustrates a method of preparing compounds of the formula I. For those compounds of the formula I wherein R² is other than hydrogen, an initial condensation reaction is carried out by reacting a substituted amine of the formula II with an appropriately functionalized beta-keto ester of the formula

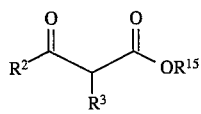

VI wherein R¹⁵ is methyl or ethyl. This reaction is generally carried out in an inert solvent such as ethyl ether, a halogenated hydrocarbon, dimethylformamide (DMF), acetonitrile or a lower alcohol, preferably ethanol, at a temperature from about ambient temperature to about the reflux temperature of the solvent, preferably from about 40° C. to about 100° C. It is preferable to remove water as it is formed in the reaction using, for example, molecular sieves, sodium sulfate, magnesium or calcium sulfate (preferably calcium sulfate), and to catalyze the reaction with a small quantity of acid (e.g., hydrochloric acid, sulfuric acid, paratoluenesulfonic acid or phosphoric acid), preferably acetic acid.

For those compounds wherein R² is hydrogen, the condensation reaction is carried out by reacting a malonate of the formula VII

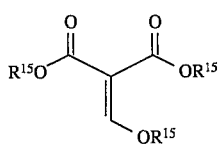

VII wherein each R¹⁵ is independently selected from methyl and ethyl, with an amine the formula II in an inert solvent, preferably toluene, at a temperature from about ambient temperature to about the reflux temperature of the solvent, preferable from about 20° C. to about 120° C.

The compound of formula III produced in the foregoing reaction may be cyclized by heating it in a high boiling, inert solvent (e.g., xylenes, mesitylene or diphenyl ether), preferably diphenyl ether/biphenyl (Dowtherm, trademark), at a temperature from about 140° C. to about 270° C., preferably about 250° C. Where substitution of the aniline of formula II is unsymmetrical, cyclization may yield a compound of the formula IV as a mixture of isomers. These isomers may be separated by a number of purification methods well known to those skilled in the art (e.g., chromatography, crystallization, etc.)

The condensation reaction using a compound of the formula VII and the subsequent cyclization reactions described above produce compounds wherein R³ is —COOR¹⁵. These esters can be converted to the corresponding carboxylic acids, and the resulting acids decarboxylated to form the corresponding compounds wherein R³ is hydrogen. The hydrolysis reaction is typically conducted using an alkali metal hydroxide in water, a lower alcohol, tetrahydrofuran (THF), acetonitrile or an aqueous mixture of these solvents. It is preferably in aqueous sodium hydroxide. Suitable temperatures for this reaction range from about room temperature to about the reflux temperature of the solvent. The reflux temperature is preferred. The decarboxylation is generally carried out by heating the acid in an inert solvent (e.g., quinaldine, diphenyl ether or mesitylene), preferably in diphenyl ether/biphenyl (Dowtherm, trademark), at a temperature from about 150° C. to about 280° C., preferably about 250° C.

Compounds of the formula IV wherein R² is hydrogen are preferably prepared by condensing the appropriate aniline of formula II with 5-(alkoxymethylene)-2,2-dimethyl-1,3-dioxane- 4,6-dione and then heating the 'so obtained 5-(anilinomethylene)- 2,2-dimethyl-1,3-dioxane-4,6-dione at 200° C. to about 270° C. according to procedures described in the literature. (See McNab et al., *J. Chem. Soc., Perkin Trans. I*, 853–868 (1988); Culbertson et al., *J. Heterocyclic Chem.*, 24, 1509–1520 (1987); Matyus et al., *Heterocycles*, 20, 2225–2228 (1983); Bihlmayer et al., *Montash. Chem.*, 98, 584–578 (1967); and British Patent 1,147,760 (1966) to Sterling Drug Inc.)

Treatment of a compound of the formula IV with phosphorus pentachloride, phosphorus oxychloride or a mixture of the two yields the corresponding compound of formula V. The reaction temperature may range from about −10° C. to about 180° C. Preferably, the compound of formula IV is treated with phosphorus oxychloride and DMF at a temperature from about 0° C. to about 75° C.

Compounds of the formula V may be converted to the corresponding compounds of formula I by reacting them with the appropriate amine of the formula HNR¹ neat or in an inert solvent such as a lower alcohol, a halogenated hydrocarbon or (DMF), preferably ethanol, at a temperature from about ambient temperature to about 180° C., depending on the reactivity of the particular amine. The preferred solvent is ethanol.

Compounds of the formula I wherein $R^5$, $R^6$ or $R^7$ is amino may be prepared by reduction of the corresponding compounds wherein $R^5$, $R^6$ or $R^7$ respectively, is nitro using methods well known in the art. (See March, "Advanced Organic Chemistry", pp. 1125–1126, McGraw-Hill Book Company, New York, 1977). It is preferable to use hydrogen gas at a pressure of about 1 atmosphere in the presence of palladium on carbon, and to conduct the reaction in a lower alcohol solvent at about room temperature.

Similarly, compounds of the formula I wherein $R^5$ is —NHC(=NR$^5$)R$^9$, —NHSO$_2$R$^{11}$, —NHCOR$^{12}$, guanidino or ureido, or wherein $R^6$ is —NHCOR$^{13}$, —NHC(=NR$^8$)R$^9$, —NHSO$_2$R$^{13}$, guanidino or ureido, or wherein $R^7$ is —NHC(=NR$^8$)R$^9$, —NHSO$_2$R$^{14}$, —NHCOR$^{14}$, ureido or guanidino, may be prepared from the corresponding amino compounds using procedures well known to those skilled in the art. (See, for the preparation of amides, March, "Advanced Organic Chemistry", pp. 392–393, McGraw-Hill Book Company, New York, 1977. See, for the preparation of sulfonamides, March, "Advanced Organic Chemistry", pp 451– 452, McGraw-Hill Book Company, New York, 1977. See, for the preparation of amidines, March, "Advanced Organic Chemistry", pp. 823–824 and p. 891, McGraw-Hill Book Company, New York, 1977. See, for the preparation of ureas, March, "Advanced Organic Chemistry", pp. 823, McGraw-Hill Book Company, New York, 1977. See, for the preparation of guanidines, Scott et al., J. Amer. Chem. Soc., 75, 4053 (1953), Bannard, R. A. B. et al., Can. J. Chem., 36, 1541 (1958) and Bodansky, M., J. Amer. Chem. Soc. 86, 4452 (1964).

Compounds of the formula I wherein $R^5$, $R^6$ or $R^7$ is hydroxy or wherein $R^5$ and $R^6$, or $R^5$ and $R^7$ are both hydroxy may be prepared by treating the corresponding methoxy compounds with concentrated hydrogen bromide or hydrogen iodide or by heating them with aluminum chloride in an appropriate solvent such as toluene heated at reflux. Alternatively, the corresponding methoxy intermediates can be treated with boron tribromide or boron tribromide-methyl sulfide complex in an appropriate solvent such as methylene chloride or 1,2-dichloroethane, as exemplified below.

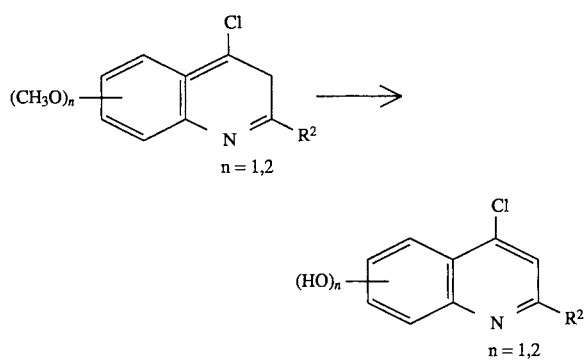

The resulting hydroxy compounds can then be reacted with the appropriate amines, as described above, to produce the desired compounds of structure I that are substituted in 5, 6 and/or 7 positions.

Compounds of the formula I wherein $R^5$ i's 5-pyrazolyl may be prepared as described in Example 17.

Except where otherwise noted, pressure is not critical in any of the above reactions. Preferred temperatures for the above reactions were stated where known. In general, the preferred temperature for each reaction is the lowest temperature at which product will be formed.

The pharmaceutically acceptable acid addition salts of compounds of the formula I are prepared in a conventional manner by treating a solution or suspension of the free base of formula I with about one chemical equivalent of a pharmaceutically acceptable acid. Conventional concentration and recrystallization techniques are employed in isolating the salts. Examples of pharmaceutically acceptable acids are acetic, lactic, succinic, maleic, tartaric, citric, gluconic, ascorbic, benzoic, methanesulfonic, cinnamic, fumaric, phosphonic, hydrochloric, hydrobromic, hydroiodic, sulfamic and sulfonic acid.

The active compounds of this invention and their pharmaceutically acceptable acid addition salts are useful in stimulating, restoring or enhancing the immune response of a host vertebrate, thus increasing the host's resistance to infection or infestation by bacteria, viruses, fungi, etc. They are therefore useful, alone or in combination with antiinfective therapy, in the prophylactic or therapeutic treatment of any infectious disease.

The activity of the compounds of this invention as immunostimulants may be determined by the following procedure.

Mice (Harlan Sprague Dawley, female) in the control group (i.e., those not receiving drug) and those in the experimental group are infected with *E. coli* 51A760 ($2\times10^7$ colony forming units) by intraperitoneal injection. (A subtherapeutic dose of gentamicin (0.5 mg/kg) may be optionally administered subcutaneously to mice in both the experimental and the control group 0.5, 4, and 24 hours after such injection). Twenty-four hours before the injection with *E. coli*, the mice in the experimental group are treated subcutaneously with drug dissolved or suspended in pyrogen-free saline. The number of surviving mice in the control and experimental groups 96 hours after such infection is recorded. A compound is considered active if the number of surviving mice in the experimental group is significantly higher than those surviving in the control group.

The compounds of this invention may be administered alone, but will generally be administered in admixture with a pharmaceutical carrier selected with regard to the intended route of administration and standard pharmaceutical practice. They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of vertebrates other than humans, compounds can be administered intramuscularly or subcutaneously at dosage levels of about 0.1–50 mg/kg/day, advantageously 0.2–10 mg/kg/day given in a single daily dose or up to 3 divided doses.

The compounds of this invention can be administered to humans for the treatment of bacterial diseases by the parenteral route. For intramuscular or intravenous administration, dosage levels are about 0.1–200 mg/kg/day, advantageously 0.5–50 mg/kg/day. While intramuscular administration may consist of a single dose or up to 3 divided doses, intravenous administration can consist of a continuous drip. Variations will necessarily occur depending on the weight and condition of the subject being treated and the particular route of administration chosen, as will be known to those skilled in the art.

The present invention is illustrated by the following examples. It will be understood, however, that the invention is not limited to the specific details of these examples. Melting points are uncorrected. Proton nuclear magnetic resonance spectra ($^1$H NMR) and $^{13}$C nuclear magnetic resonance spectra ($^{13}$C NMR) were measured for solutions in deuterodimethylsulfoxide (d$_6$-DMSO) and peak positions are expressed in parts per million (ppm) downfield from tetramethylsilane (TMS). The peak shapes are denoted as follows: s, singlet; d, doublet, t, triplet; q, quartet; m, multiplet; br, broad; c, complex.

EXAMPLE 1

9-(m-Anisidino]-7-methyl-1H-pyrazolo]3,4-f]quinoline hydrochloride

A. 9-Hydroxy-7-methyl-1H-pyrazolo[3,4-f]quinoline

To a suspension of 6-aminoindazole (40.0 g, 0.30 mol) in absolute ethanol (500 ml) was added ethyl acetoacetate (70.37 g, 54 mol), calcium sulfate (CaSO$_4$) (20 g) and acetic acid (2 ml). The reaction mixture was heated to reflux and after 24 hours more calcium sulfate (10 g) and ethyl acetoacetate (19 ml) was added and the reflux continued for another 24 hour period. It was necessary to add more CaSO$_4$ (5 g) and ethyl acetoacetate (10 ml) and to reflux the reaction mixture for an additional 24 hours to complete the conversion of 6-aminoindazole to product. The solid was removed by filtration and the filtrate subjected to rotary evaporation. Ethanol was added and the slurry cooled in a refrigerator. The solid was collected by filtration, washed with hexanes and dried in a vacuum oven to give the cyclization precursor ethyl 3-(indazol-6-ylamino)but-2-enoate as a light brown solid (62.19 g, 84%).

A fraction of this material (30.00 g, 0.12 mol) was added to boiling diphenyl ether/biphenyl, (Dowtherm trademark), (i.e., a mixture of biphenyl and diphenylether) (600 ml) in portions. Upon completion of the addition, the reaction was continued for an additional 6 minutes. On cooling the reaction a precipitate formed which was collected by filtration and washed thoroughly with hexanes to give 9-hydroxy-7-methyl-1H-pyrazolo[3,4-f]quinoline as a tan solid (23 g, 94%).

$^1$H NMR: δ 2.40 (s, 3H), 6.i0 (s, 1H), 7.22 (d, 1H, J=8), 7.84 (d, 1H, J=S), 8.08 (s, 1H).

B. 9-Chloro-7-methyl-1H-pyrazolo[3.4-f]quinoline

To a suspension of 9-hydroxy-7-methyl-1H-pyrazolo[3,4-f] quinoline (8.00 g, 0.04 mmol) in phosphorus oxychloride (61.6 g, 0.40 mol) was added slowly N,N-dimethylformamide (40 ml). After the addition was complete, the reaction mixture was warmed to 80° C. for 1 hour and then allowed to cool to room temperature. The reaction was poured onto ice and dissolved in water (2 L total volume) and neutralized to pH 7 with 20% sodium hydroxide (NaOH). The precipitate which formed upon neutralization was collected by filtration, washed with water and dried under vacuum to give 9-chloro-7-methyl-1H-pyrazolo[3,4-f]quinoline as a white solid (8.07 g, 92%).

$^1$H NMR: δ 2.66 (s, 3H), 7.61 (d, 1H, J=9), 7.72 (s, 1H), 8.07 (d, 1H, J=9), 8.33 (s, 1H).

C. 9-(m-Anisidino)-7-methyl-1H-pyrazolo[3,4-f] quinoline hydrochloride

To a solution of 9-chloro-7-methyl-1H-pyrazolo[3,4-f] quinoline (1.63 g, 7.5 mmol) in ethanol (60 ml) was added m-anisidine (1.11 g, 9.0mmol) and the mixture was heated at reflux overnight. The solvent was removed by rotary evaporation and the residue redissolved in methanol and treated with decolorizing carbon. After filtration through diatomaceous earth (Celite™), the filtrate was subjected to rotary evaporation and the resulting pale yellow solid recrystallized from methanol/ethyl ether to give. 9-(m-anisidino)-7-methyl-1H-pyrazolo[3,4-f]quinoline hydrochloride (2.35 g, 92%) as pale yellow needles.

$^1$H NMR: δ 2.72 (s, 3H), 3.85 (s, 3H), 7.05 (d, 1H, J=8), 7.12 (s, 1H), 7.14–7.18 (m, 2H), 7.50 (t, 1H, J=8), 7.72 (d, 1H, J=9), 8.34 (d, 1H, J=9), 8.84 (s, 1H).

M.S.: m/e 304 (M$^+$, 100).

Analysis: Calc'd for C$_{18}$H$_{16}$N$_4$O.HCl.1.5H$_2$O: C, 58.78; H, 5.48; N, 15.23%. Found: C, 59.19; H, 5.51; N, 14.96%.

The title compound of Examples 2–6 were prepared by reaction of 9-chloro-7-methyl-1H-pyrazolo[3,4-f]quinoline with the requisite aniline derivative according to the procedure described in Example 1.

EXAMPLE 2

9-(p-Cyclohexylmethoxyanilino)-7-methyl-1H-pyrazolo[3,4-f] quinoline hydrochloride $^1$H NMR: δ 1.1–1.4 (m, 5H), 1.7–2.0 (m, 6H), 2.64 (s, H), 3.83 (d, 2H, J=6), 6.86 (s, 1H), 7.10 (d, 2H, J=9), 7.45 (d, 2H, J=9), 7.69 (d, 1H, J=9), 8.30 (d, 1H, J=9),8.83 (s, 1H).

M.S.: m/e 386 (M$^+$, 40)

High Resolution Mass Spectrum: Calc'd for C$_{24}$H$_{26}$N$_4$O: 386.2107 Found: 386.2077.

EXAMPLE 3

9- (p-Butoxyanilino)-7-methyl-1H-pyrazolo[3,4-f]quinoline hydrochloride $^1$H NMR: δ 0.96 (t, 3H, J=6), 1.46 (m, 2H), 1.72 (m, 2H), 2.66 (s, 3H), 4.04 (t, 2H, J=6), 6.86 (s, 1H), 7.11 (d, 2H, J=9), 7.46 (d, 2H, J=9), 7.70 (d, 1H, J=8), 8.30 (d, 1H, J=8), 8.82 (s, 1H).

M.S.: m/e 346 (M$^+$, 90).

EXAMPLE 4

9-(p-Chloroanilino)-7-methyl-1H-pyrazolo[3,4-f]quinoline hydrochloride $^1$H NMR: δ 2.68 (s, 3H), 7.06 (s, 1H), 7.62 (m, 4H), 7.68 (d, 1H, J=9), 8.28 (d, 1H, J=9), 8.80 (s, 1H).

M.S.: m/e 309 (M$^+$, 100)

Analysis: Calc'd for C$_{17}$H$_{13}$N$_4$Cl.HCl.H$_2$O: C, 56.21; H, 4.44; N, 15.42%. Found: C, 56.21; H, 4.40; N, 15.24%.

EXAMPLE 5

9-(p-Benzyloxyanilino)-7-methyl-1H-pyrazolo[3,4-f] quinoline hydrochloride $^1$H NMR: δ 2.64 (s, 3H), 5.18 (s, 2H), 6.86 (s, 1H), 7.19 (d, 2H, J=8), 7.3–7.5 (m, 7H), 7.65 (d, 1H, J=10), 8.28 (d, 1H, J=10), 8.80 (s, 1H).

M.S.: m/e 380 (M$^+$, 25 )

Analysis (free base): Calc'd for C$_{24}$H$_{20}$N$_4$O.0.5H$_2$O: C, 74.02; H, 5.44; N, 14.39%. Found: C, 74.32; H, 5.08; 14.26%.

EXAMPLE 6

9-(p-Hydroxyanilino)-7-methyl-1H-pyrazolo[3,4-f]quinoline hydrochloride $^1$H NMR: δ 2.66 (s, 3H), 6.84 (s, 1H), 6.96 (d, 2H, J=8), 7.34 (d, 2H, J=8), 7.66 (d, 1H, J=10), 8.30 (d, 1H, J=10), 8.82 (s, 1H).

M.S.: m/e 290(M⁺, 100)

Analysis: Calc'd for $C_{17}H_{14}N_4O \cdot HCl$: C, 62.48; H, 4.63; N, 17.14%. Found: C, 61.91; H, 4.43; N, 16.93%.

EXAMPLE 7

9-(Cyclohexylamino)-7-methyl-1H-pyrazolo[3,4-f]quinoline hydrochloride.

9-Chloro-7-methyl-1H-pyrazolo[3,4-f]quinoline (0.44 g, 2.0 mmol) and cyclohexylamine (0.79 g, 8.0 mmol) were placed in a sealable reaction vessel which was flushed with nitrogen and then sealed. The reaction was placed in a ° C. bath and heated overnight. The excess cyclohexylamine was removed by rotary evaporation and the residue dissolved in methanol and treated with decolorizing carbon. After filtration through diatomaceous earth (Celite™), the methanol was removed by rotary evaporation and the residue partitioned between ethyl acetate and aqueous potassium hydroxide (KOH). The organic layer was washed with water and dried over sodium sulfate ($Na_2SO_4$), and the solvent was removed by rotary evaporation to give a white solid. The solid was washed with ether giving 9-(cyclohexylamino)-7-methyl- 1H-pyrazolo[3,4-f]quinoline as white needles (0.38 g, 68%). The free base was converted to the corresponding hydrochloride salt by treatment with anhydrous hydrogen chloride (HCl)/ether.

¹H NMR: δ 1.3–2.2 (m, 10H), 2.74 (s, 3H), 4.0 (br s, 1H), 7.12 (s, 1H), 7.64 (d, 1H, J=8), 8.26 (d, 1H, J=8), 8.80 (s, 1H), 9.41 (d, 1H, J=6).

M.S.: m/e 280(M⁺, 55).

Analysis: Calc'd for $C_{17}H20N_4 \cdot HCl$: C, 64.45; H, 6.68; N, 17.68%. Found: C, 63.98; H,. 6.46; N, 17.43%.

EXAMPLE 8

9-(m-Anisidino)-7-methyl-1H-triazolo[3,4-f]quinoline hydrochloride

The title compound was prepared by the method described in Example 1 with the modification that 5-aminobenzotriazole was used as the starting material instead of 6-aminoindazole.

¹H NMR: δ 2.76 (s, 3H), 4.85 (s, 3H), 7.00 (d, 1H, J=8), 7.20 (apparent s, 3H), 7.50 (t, 1H, J=8), 8.19 (d, 1H, J=9), 8.44 (d, 1H, J-9).

High resolution Mass Spectrum: Calc'd for $C_{17}H_{15}N_5O$: 305.1277. Found: 305.1278.

EXAMPLE 9

9-(m-Anisidino)-1H-pyrazolo[3,4-f]quinoline hydrochloride

A. Ethyl 3-N-(6-indazolyl)amino-2-ethoxycarbonyl-2-propenoate

6-Aminoindazole (10.00 g, 75 mmol) was suspended in toluene (150 ml) to which diethyl ethoxymethylenemalonate (19.45 g, 90 mmol) was then added and the reaction mixture was heated to reflux. After 3 hours the heat was removed and the reaction mixture was stirred at room temperature overnight. The solvent was removed by rotary evaporation and the residue triturated with hexanes. The tan solid was collected by filtration, washed with hexanes and air dried to give the expected product ethyl 3-N-(6-indazolyl)amino-2-ethoxycarbonyl- 2-propenoate (19.26 g, 85%).

¹H NMR: δ 1.2 (overlapping t, 6H), 4.15 (overlapping q, 4H), 7.08 (d, 1H, J=6), 7.42 (s, 1H), 7.70 (d, 1H, J=6), 7.98 (s, 1H), 8.42 (overlapping s, 2H).

B. 8-Carboxy-9-hydroxy-1H-pyrazolo[3,4-f]quinoline

To boiling diphenyl ether/biphenyl, (Dowtherm, trademark), (320 ml) was added ethyl 3-N-(6-indazolyl)amino-2-ethoxycarbonyl-2-propenoate (17.26. g, 57 mmol) portionwise. After the addition was complete the reaction was continued for an additional 15 minutes and then allowed to cool to room temperature. The precipitate which formed upon cooling was collected by filtration and washed thoroughly with hexanes to give 8-carboethoxy-9-hydroxy-1H-pyrazolo[ 3,4-f]quinoline as a light brown powder (13.31 g, 91%).

A mixture of 8-carboethoxy-9-hydroxy-1H-pyrazolo[3,4-f] quinoline (12.31 g, 47.8 mmol) and 10% aqueous sodium hydroxide (96 ml) was refluxed for 8 hours, at which time the dark-colored solution was treated with decolorizing carbon and filtered through diatomaceous earth (Celite™). The filtrate was neutralized with 6M HCl and the resulting precipitate isolated by filtration. The light brown solid was air dried to give 8-carboxy-9-hydroxy-1H-pyrazolo[3,4-f] quinoline (10.08 g, 92%).

¹H NMR: δ 7.48 (d, 1H, J=8), 8.19 (d, 1H, J=8), 8.26 (s, 1H), 8.90 ( s, 1H).

C. Hydroxy-1H-pyrazolo[3,4-f]quinoline

A mixture of 8-carboxy-9-hydroxy-1H-pyrazolo[3,4-f]quinoline (5.00 g, 21.8 mmol) and quinaldine (50 ml) were refluxed for 20 hours. After cooling, the precipitate was collected by filtration and washed thoroughly with ether to give 9-hydroxy-1H-pyrazolo[3,4-f]quinoline (2.97 g, 74%).

¹H NMR: δ 6.24 (d, 1H, J=7), 7.24 (d, 1H, J=9), 7.96 (m, 2H), 8.10 (s, 1H).

D. 9-Chloro-1H-pyrazolo[3,4-f]quinoline

A mixture of 9-hydroxy-1H-pyrazolo[3,4-f]quinoline (2.97 g, 16.0 mmol) and phosphorus oxychloride (24.58 g, 160 mmol) at 0° C. was treated with dimethylformamide (DMF) (15.4 ml) dropwise. After addition was complete, the viscous reaction mixture was allowed to warm to room temperature and stirred overnight. The mixture was then poured onto ice and the resulting dark brown solution was treated with decolorizing carbon and filtered, and the brown filtrate neutralized with 10M NaOH. The light brown solid which resulted was collected by filtration and air dried giving 9-chloro- 1H-pyrazolo[3,4-f]quinoline (1.73 g, 53%).

¹H NMR: d 7.65 (d, 1H, J=9), 7.76 (d, 1H, J=5), 8.08 (d, 1H, J=9), 8.34 (s, 1H), 8.78 (d, 1H, J=5).

E. 9-(m-Anisidino)-1H-pyrazolo[3,4-f]quinoline hydrochloride

To a suspension of 9-chloro-1H-pyrazolo[3,4-f]quinoline (1.10 g, 5.4 mmol) in absolute ethanol (50 ml) was added m-anisidine (0.79 ml, 7.1 mmol) and the reaction mixture heated at reflux for 48 hours. The solvent was removed by rotary evaporation and the residue was dissolved in boiling methanol, treated with decolorizing carbon and filtered to give a light yellow solution. The solvent was removed by rotary evaporation and the residue was recrystallized from methanol/ether to give 9-(m-anisidino)-1H-pyrazolo[3,4-f] quinoline hydrochloride (1.04 g, 59%) as off-white crystals.

1H NMR: δ 3.86 (s, 3H), 6.98 (d, 1H, J=6), 7.16 (m, 2H), 7.22 (d, 1H, J=6), 7.48 (t, 1H, J=6), 7.68 (d, 1H, J=9), 8.30 (d, 1H, J=9), 8.50 (d, 1H, J=6), 8.84 (s, 1H).

M.S.: m/e 290 (M⁺, 100).

Analysis (mesylate salt): Calc'd for $C_{14}H_{14}N_4O \cdot CH_3SO_3H$: C, 55.55; H, 4.57; N, 14.16%. Found: C, 55.95; H, 4.70; N, 4.50%.

The title compound of Examples 10 and 11 were prepared by reaction of 9-chloro-1H-pyrazolo[3,4-f]quinoline with the requisite aniline derivative according to the procedure described in Example 9.

EXAMPLE 10

9-(p-Cyclohexylmethoxyanilino)-1H-pyrazolo[3,4-f]quinoline hydrochloride $^1$H NMR: δ 0.9–1.3 (m, 5H), 1.6–1.9 (m, 6H), 4.82 (d, 2H, J=6), 6.94 (br s, 1H), 7.08 (d, 2H, J=7), 7.44 (d, 2H, J=7), 7.68 (br s, 1H), 8.30 (d, 1H, J=8), 8.46 (br s, 1H), 8.82 (br s, 1H).

M.S.: m/e 371 (M$^+$, 30)

EXAMPLE 11

9-(p-Chloroanilino)-1H-pyrazolo[3,4-f]quinoline hydrochloride $^1$H NMR: δ 7.18 (d, 1H, J=7), 7.6–7.7 (m, 5H), 8.37 (d, 1H, J=9), 8.54 (d, 1H, J=7), 8.87 (s, 1H).

M.S.: m/e 2.4 (M$^+$, 100)

EXAMPLE 12

6-Amino-4-(p-butoxyanilino)-2-phenylquinoline hydrochloride

A. 4-Chloro-6-nitro-2-phenylquinoline

4-Hydroxy-6-nitro-2-phenylquinoline (10.00 g, 38 mmol) was suspended in phosphorus oxychloride (POCl$_3$) (57.58 g, 380 Mol) at 0° C. Dimethylformamide (DMF) (45 ml) was added dropwise and the resulting mixture heated at 70° C. for 5 hours. The reaction was cooled and then poured onto ice. The pH was adjusted to 6 with aqueous sodium hydroxide and the precipitate collected by vacuum filtration and dried in a vacuum oven to give 4-chloro-6-nitro-2-phenylquinoline (10.95 g, 102%) as a yellow powder.

M.P.: 166°–167° C.

$^1$H NMR: δ 7.5–7.6 (m, 3H), 8.3–8.4 (m, 3H), 8.52 (s, 1H), 8.61 (dd, 1H, J=9, 3), 9.10 (d, 1H, J=3).

B. 4-(p-Butoxyanilino)-6-nitro-2-phenylquinoline

To a suspension of 4-chloro-6-nitro-2-phenylquinoline (0.57 g, 2.0 mmol) in absolute ethanol (25 ml) was added 4-butoxyaniline (0.40 g, 2.4 mmol), and the mixture was heated at reflux for 4 hours. The solvent was removed by rotary evaporation and the residue was redissolved in methanol, treated with decolorizing carbon and filtered through diatomaceous earth (Celite™). The solvent was removed by rotary evaporation. The residue was recrystallized from methanol/ether to give 4-(p-butoxy)-6-nitro-2-phenylquinoline (0.61 g, 69%).

$^1$H NMR: δ 1.00 (t, 3H, J=6), 1.5 (m, 2H), 1.75 (m, 2H), 4.08 (t, 2H, J=6), 7.00 (s, 1H), 7.18 (d, 2H, J=9), 7.50 (d, 2H, J=9), 7.63 (m, 3H), 7.96 (d, 2H, J=6), 8.54 (d, 1H, J 8), 8.76 (d, 1H, J=8), 9.84 (s, 1H).

C. 6-Amino-4-(p-butoxyanilino]-2-phenylquinoline hydrochloride

To a suspension of 4-(p-butoxy)-6-nitro-2-phenylquinoline (0.42 g, 0.94 mmol) in methanol (25 ml) was added ammonium formate (0.59 g, 9.4 mmol) and, finally, 10% palladium on carbon (Pd/C) (50 mg), and the mixture heated at reflux for 1.5 hours. The reaction was filtered warm through diatomaceous earth (Celite™) and the solvent was removed by rotary evaporation. The remaining solid was washed thoroughly with water and then recrystallized from methanol/ether. The resulting yellow crystals (0.16 g, 40%) were dissolved in methanol (10 ml) and treated with HCl in ether (1M, 8 ml). The solvent was removed and the residue recrystallized twice from methanol/ether to give 6-amino-4-(p-butoxyanilino)-2-phenylquinoline hydrochloride (0.08 g, 48%) as a yellow solid.

$^1$H NMR: δ 1.00 (t, 3H, J=6), 1.48 (m, 2H), 1.76 (m, 2H), 4.06 (t, 2H, J=5), 6.76 (s, 1H), 7.12 (d, 2H, J=9), 7.44 (d, 2H, J=9), 7.52 (d, 1H, J=6), 7.6–7.7 (m, 4H), 7.84 (d, 2H, J=6), 8.16 (d, 1H, J=9).

M.S.: m/e 383 (M$^+$, 70)

Analysis: Calc'd for C$_{25}$H$_{25}$N$_3$O.2HCl.H$_2$O: C, 63.29; H, 6.16; N, 8.86%. Found: C, 62.91; H, 6.36; N, 8.63%.

The title compounds of Examples 13–15 were prepared by reaction of 4-chloro-6-nitro-2-phenylquinoline with the requisite aniline derivative according to the procedure described in Example 12.

EXAMPLE 13

6-Amino-4-(p-cyclohexylmethoxyanilino)-2-phenylquinoline hydrochloride $^1$H NMR: δ 1.1–1.2 (m, 5H), 1.6–1.8 (m, 6H), 3.81 (d, 2H, J=6), 6.70 (s, 1H), 7.07 (d, 2H, J=9), 7.4–7.5 (m, 3H), 7.5–7.6 (m, 4H), 7.78 (d, 2H, J=8), 8.07 (d, 1H, J=9), (s, 1H).

M.S.: m/e 423 (M$^+$, 60).

Analysis: Calc'd for C$_{28}$H$_{29}$N$_3$O.2HCl.0.5H$_2$O: C, 66.53; H, 6.38; N, 8.31%. Found: C, 66.54; H, 5.93; N, 8.0%.

EXAMPLE 14

6-Amino-4-(p-chloroanilino)-2-phenylquinoline hydrochloride $^1$H NMR: δ 6.94 (s, 1H) 7.5–7.6 (m, 9H), 7.86 (d, 2H, J=6), 8.14 (d, 1H, J=9), 10.44 (s, 1H).

M.S.: m/e 345 (M$^+$, 100).

Analysis: Calc'd for C$_{21}$H$_{16}$N$_3$Cl.2H$_2$O.1.5HCl: C, 57.32; H, 4.49; N, 9.40%. Found.: C, 57.78; H, 4.96; N, 9.63%.

EXAMPLE 15

6-Amino-4-(p-anisidino)-2-phenylquinoline hydrochloride $^1$H NMR: δ 3.80 (s, 3H), 7.08 (d, 2H, J=8), 7.43 (d, 2H, J=8), 7.5–7.8 (m, 7H), 8.13 (d, 1H, J=9), 10.42 (s, 1H).

M.S.: m/e 341 (M$^+$, 100).

Analysis: Calc'd for C$_{22}$H$_{19}$N$_3$O.2HCl.1.5H$_2$O: C, 59.87; H, 5.48; N, 9.08%. Found: C, 59.66; H, 5.44; N, 9.52%.

EXAMPLE 16

4-(p-Cyclohexylmethoxyanilino)-6-methylsulfonamido-2-phenylquinoline hydrochloride To a suspension of 6-amino-4-(p-cyclohexylmethoxyanilino)-2-phenylquinoline hydrochloride (0.21 g, 0.5 mmol) in anhydrous THF (10 ml) at 0° C. was added methanesulfonyl chloride (69 mg, 0.6 mmol) followed by addition of triethylamine (61 mg, 0.6 mmol). The reaction mixture was allowed to warm slowly to room temperature and stirred overnight. The solvent was removed by rotary evaporation and the residue partitioned between ethyl acetate (EtOAc) and 1M hydrochloric acid. The layers were separated, the organic layer was washed with saturated sodium bicarbonate and dried (Na$_2$SO$_4$) and the solvent was removed by rotary evaporation. The crude material was dissolved in warm methanol and treated with 1M HCl in ether. After 2 hours at room temperature, the solvent was removed by rotary evaporation and the residue recrystallized from methanol/ether to give 4-(p-cyclohexylmethoxyanilino)-6-methylsulfonamido-2-phenylquinoline hydrochloride (38%) as a pale yellow solid.

$^1$H NMR: δ 0.9–1.3 (m, 5H), 1.6–1.8 (m, 6H), 3.24 (s, 3H), 3.82 (d, 2H, J=6), 6.78 (s, 1H), 7.09 (d, 2H, J=9), 7.44 (d, 2H, J=9), 7.6 (m, 3H), 7.83 (m, 3H), 8.34 (m, 2H).

M.S.: m/e 502 (M$^+$, 10).

EXAMPLE 17

4-(m-Anisidino)-2-methyl-6-(5-pyrazolo)quinoline hydrochloride

A. 4-Nitrobenzoylacetaldehyde

To a solution of 4-nitroacetophenone (8.26 g, 50 mmol) in anhydrous tetrahydrofuran (THF) at 0° C. was slowly added sodium ethoxide in ethanol (prepared from 1.27. g (55 mmol) sodium in 26 ml ethanol) followed by addition of ethyl formate (5.56 g, 75 mmol). The reaction was allowed to slowly warm to room temperature and stir overnight. The reaction was diluted with water (800 ml) and washed with ether. The aqueous layer was acidified (pH 1–2) with concentrated hydrochloric acid (HCl) and the mixture extracted with ethyl acetate. The combined organic layers were dried (Na$_2$SO4) and the solvent was removed by rotary evaporation to give 4-nitrobenzoylacetaldehyde (2.69 g, 28%) as an orange solid.

$^1$H NMR (CDCl$_3$): δ 6.24 (d, 1H, J=3), 8.02 (d, 2H, J=9), 8.28 (d, 2H, J=9), 8.44 (d, 1H, J=3).

B. 4-(5-Pyrazoyl)nitrobenzene

To a suspension of 4-nitrobenzoylacetaldehyde (2.75 g, 14.2 mmol) in methanol (100 ml) at 0° C. was added hydrazine hydrate (0.50 g, 15.7 mmol). The resulting burgundy solution was stirred at 0° C. for 2.5 hours, at which time the solvent was removed by rotary evaporation and the residue was partitioned between water and ethyl acetate. The aqueous layer was extracted with more ethyl acetate and the combined organics were then washed with saturated sodium chloride (NaCl) and dried (Na$_2$SO$_4$), and the solvent was removed by rotary evaporation to give 4-(5pyrazoyl)nitrobenzene (2.32 g, 86%) as an orange solid.

$^1$H NMR: δ 6.90 (s, 1H), 7.84 (s, 1H), 8.04 (d, 2H, J=9), 8.22 (d, 2H, J=9).

C. 4-Hydroxy-2-methyl-6-(5-pyrazolyl)quinoline

To a suspension of 4-(5-pyrazoyl)nitrobenzene (1.25 g, 6.6 mmol) in methanol (60 ml) was added 10% Pd/C (0.13 g) and the mixture shaken under hydrogen (45 psi) for 2 hours. The reaction was filtered through diatomaceous earth (Celite™) and the solvent was removed by rotary evaporation to give 4-(5-pyrazoyl)aniline as a brown oil which was used directly in the next reaction.

To a solution of 4-(5-pyrazoyl)aniline (1.05 g, 6.6 mmol) in absolute ethanol (20 ml) was added ethyl acetoacetate (1.72 g, 13.2 mmol), calcium sulfate (2.0 g) and a few drops of acetic-acid, and the mixture was heated at reflux for 48 hours, with more calcium sulfate (2.0 g) and ethyl acetoacetate (0.85 g) added after 12 and 36 hours. The reaction was then cooled to room temperature, filtered, and the solvent was removed by rotary evaporation. The residue was triturated with several portions of methanol, the methanol fractions were combined and the solvent was removed by rotary evaporation. The residue was chromatographed (silica gel, 20% ethyl acetate (EtOAc) in methylene chloride (CH$_2$Cl$_2$) to 5% methanol (CH$_3$OH) in EtOAc) to give the condensation product as a yellow oil (0.11 g, 7%). This was cyclized by adding it portionwise to boiling diphenyl ether/biphenyl, (Dowtherm, trademark), (10 ml). After the addition was complete, the reaction was continued for an additional 10 minutes and then allowed to cool to room temperature. The precipitate which formed was collected by filtration, washed well with hexanes and dried under vacuum to give 4-hydroxy-2-methyl-6-(5-pyrazoyl)quinoline (63%) as a brown solid.

$^1$H NMR: δ 2.32 (s, 3H), 5.90 (s, 1H), 6.72 (s, 1H), 7.50 (d, 1H, J=7), 7.78 (s, 1H), 8.06 (d, 1H, J=7), 8.38 (s, 1H).

M.S.: m/e 225 (M$^+$, 100)

D. 4-Chloro-2-methyl-6-(5-pyrazoyl)quinoline

To a suspension of 4-hydroxy-2-methyl-6-(5-pyrazoyl)quinoline (0.13 g, 0.55 mmol) in phosphorus oxychloride (0.85 g, 5.5 mmol) cooled in a water bath was added DMF (5 ml) dropwise and the reaction mixture was stirred at room temperature overnight. The reaction mixture was poured onto ice and the solution neutralized with 10N NaOH. The precipitate which formed was filtered, washed with water and dried under vacuum to give 4-chloro-2-methyl 6-(5-pyrazoyl)quinoline (0.12 g, 86%) as light brown solid.

$^1$H NMR: δ 2.66 (s, 3H), 6.86 (s, 1H), 7.70 (s, 1H), 7.84 (s, 1H), 8.00 (d, 1H, J=8), 8.28(d, 1H, J=8), 8.50 (s, 1H).

E. 4-(m-Anisidino)-2-methyl-6-(5-pyrazoyl)quinoline hydrochloride

To a solution of 4-chloro-2-methyl-6-(5-pyrazoyl)quinoline (0.10 g, 0.41 mmol) in absolute ethanol (7.5 ml) was added m-anisidine (61 mg, 0.49 mmol) and the reaction was refluxed overnight. The solvent was removed by rotary evaporation. The residue was redissolved in methanol, treated with decolorizing carbon and filtered through diatomaceous earth (Celite™). The solvent was then removed by rotary evaporation. The crude product was recrystallized from methanol/ether to give 4-(m-anisidino)-2-methyl-6-(5-pyrazoyl) quinoline hydrochloride (92 mg, 61%) as yellow needles.

$^1$H NMR: δ 2.60 (s, 3H), 3.81 (s, 3H), 6.74 (s, 1H), 6.98 (d, 1H, J=8), 7.05 (m, 3H), 7.47 (t, 1H, J=8), 7.86 (s, 1H), 8.05 (d, 1H, J=8), 8.46 (d, 1H, J=8), 9.16 (s, 1H).

M.S.: m/e 330 (M$^+$, 100)

Analysis: Calc'd for C$_{20}$H$_{18}$N$_4$O.HCl.0.25H$_2$O: C, 64.69; H, 5.29; N, 15.09%. Found: C, 64.58; H, 5.01; N, 15.10%.

EXAMPLE 18

4-(p-Cyclohexylmethoxyanilino)-2-methyl-6-(5-pyrazolo)quinoline hydrochloride

4-Chloro-2-methyl-6-(5-pyrazoyl) quinoline was treated with p-cyclohexylmethoxyaniline using the procedure described in Example 17 to give 4-(p-cyclohexylinethoxyanilino)-2-methyl-6-(5-pyrazolo)quinoline hydrochloride.

$^1$H NMR: δ 1.0–1.3 (m, 5H), 1.6–1.9 (m, 6H), 2.48 (s, 3H), 3.84 (d, 2H, J=6), 6.52 (s, 1H), 7.02 (s, 1H), 7.08 (d, H, J=9), 7.36 (d, 2H, J=9), 7.86 (br s, 1H), 7.98 (d, 1H, J=7), 8.42 (d, 1H, J=7), 9.10 (s, 1H).

M.S.: m/e 412 (M$^+$, 15)

High Resolution Mass Spectrum: Calc'd for C$_{20}$H$_{18}$N$_4$O: 412.2263. Found: 412.2243.

The following compounds were prepared by a procedure similar to that of Example 6.

EXAMPLE 19

9-(4-Ethylanilino)-7-methyl-1H-pyrazolo[3,4-f]quinoline mesylate $^1$H NMR: δ 1.24 (t, 3H, J=7), 2.6–2.7 (m, 5H), 7.04 (s, 1H), 7.42 (d, 2H, J=8), 7.48 (d, 2H, J=e), 7.53 (d, 1H, J=9), 8.34 (d, 1H, J=9), 8.86 (s, 1H).

M.S.: m/e 302 (M$^+$, 95)

Analysis: Calc'd for C$_{19}$H$_{18}$N$_4$.CH$_3$SO$_3$H.0.75H$_2$O: C, 58.31; H 5.75; N, 13.60%. Found: C, 58.30; H, 5.37; N, 16.21%.

EXAMPLE 20

7-Methyl-9-(4-propylanilino)-1H-pyrazolo[3,4-f]quinoline hydrochloride $^1$H NMR: δ 0.93 (t, 3H, J=7), 1.64 (m, 2H), 2.53 (m, 5H), 7.02 (s, 1H), 7.39 (d, 2H, J=8), 7.47 (d, 2H, J=8), 7.70 (d, H, J=9), 8.31 (d, 1H, J=9), 8.83 (s, 1H).

M.S.: m/e 316 (M$^+$, 70)

Analysis: Calc'd for C$_{20}$H$_{20}$N$_4$.HCl.H$_2$O: C, 64.77; H, 6.25; N, 15.11%. Found: C, 64.43; H, 6.03; N, 14.89%.

EXAMPLE 21

7-Methyl-9-(4-toluidino)-1H-pyrazolo[3,4-f]quinoline hydrochloride $^1$H NMR: d 2.42 (s, 3H), 2.70 (s, 3H), 7.01 (s, 1H), 7.41 (d, 2H, J=8), 7.44 (d, 2H, J=8), 7.72 (d, 1H, J=9), 8.34 (d, 1H, J=9), 8.86 (s, 1H).

M.S.: m/e 288 (M$^+$, 100)

Analysis: Calc'd for C$_{18}$H$_{16}$N$_4$.HCl.H$_2$O: C, 63.06; H, 5.59; N, 16.34%. Found: C, 62.90; H, 5.37; N, 16.21%.

EXAMPLE 22

9-cyclopentylamino-7-methyl-1H-pyrazolo[3,4-f]quinoline mesylate

The title compound was prepared as described for Example 7 except that cyclopentylamine was used instead of cyclohexylamine.

$^1$H NMR: d 2.6–2.8 (m, 6H), 2.2 (m, 2H), 2.32 (s, 3H), 2.–68 (s, 3H), 4.34 (m, 1H), 7.04 (s, 1H), 7.44 (d, 1H, J=9), 8.24 (d, 1H, J=9), 8.78 (s, 1H).

M.S.: m/e 266 (M$^+$, 95)

Analysis: Calc'd for C$_{16}$H$_{18}$N$_4$.CH$_3$SO$_3$H.0.25H$_2$O: C, 55.66; H, 6.18; N, 15.27%. Found: C, 55.53; H, 5.96; N, 15.20%.

The title compounds of Examples 23–28 were prepared by a procedure similar to that described in Example 1.

EXAMPLE 23

9-(4-Ethoxyanilino)-1H-pyrazolo[3,4-f]quinoline mesylate $^1$H NMR: δ 1.38 (t, 3H, J=6), 2.32 (s, 3H), 4.12 (q, 2H, J=6), 7.00 (d, 1H, J=6), 7.14 (d, 2H, J=8), 7.50 (d, 2H, J=8), 7.58 (d, 1H, J=9), 8.36 (d, 1H, J=9), 8.50 (d, 1H, J=6), 8.88 (s, 1H).

M.S.: m/e 304 (M$^+$, 95)

EXAMPLE 24

9-(4-Ethylanilino)-1H-pyrazolo[3,4-f]quinoline mesylate $^1$H NMR: δ 1.24 (t, 3H, J=7), 2.34 (s, 3H), 2.70 (q, 2H, J=7), 7.14 (d, 1H, J=7), 7.42 (d, 2H, J=7), 7.48 (d, 2H, J=7), 7.56 (d, 1H, J=9), 8.36 (d, 1H, J=9), 8.50 (d, 1H, J=6), 8.88 (s, 1H).

M.S.: m/e 288 (M$^+$, 95)

Analysis: Calc'd for C$_{18}$H$_{16}$N$_4$.CH$_3$SO$_3$H.1.25H$_2$O: C, 56.08; H, 5.57; N, 13.77%. Found: C, 55.72; H, 4.89; N, 13.57%.

EXAMPLE 25

9-(4-Propylamino)-1H-pyrazolo[3,4-f]quinoline mesylate $^1$H NMR: δ 0.94 (t, 3H, J=7), 1.62 (m, 2H), 2..36 (s, 3H), 2.64 (t, 2H, J=7), 7.12 (d, 1H, J=8),. 7.40 (d, 2H, J=6), 7.48 (d, 2H, J=6), 7.56 (d, 1H, J=9), 8.36 (d, 1H, J=9), 8.50 (br d, 1H), 8.88 (s, 1H).

M.S.: m/e 302 (M$^+$, 80)

Analysis: Calc'd for C$_{19}$H$_{18}$N$_4$.CH$_3$SO$_3$H.0.5H$_2$O: C, 58.95; H, 5.69; N, 13.75%. Found: C, 59.15; H, 5.32; N, 13.63%.

EXAMPLE 26

9-(4-Butylanilino)-1H-pyrazolo[3,4-f]quinoline mesylate $^1$H NMR: δ 0.96 (t, 3H, J=6), 1.35 (m, 2H), 1.62 (m, 2H), 2.36 (s, 3H), 2.68 (t, 2H, J=6), 7.16 (d, 1H, J=7), 7.44 (d, 2H, J=7), 7.50 (d, 2H, J=7), 7.60 (d, 1H, J=9), 8.40 (d, 1H, J=9), 8.54 (br d, 1H, J=7), 8.92 (s, 1H).

M.S.: m/e 316 (M$^+$, 70)

EXAMPLE 27

9-(p-Toluidino)-1H-pyrazolo[3,4-f]quinoline hydrochloride $^1$H NMR: δ 2.40 (s, 3H), 7.08 (d, 2H, J=7), 7.38 (d, 2H, J=7), 7.46 (d, 2H, J=7), 7.70 (d, 1H, J=9), 8.34 (d, 1H, J=9), 8.48 (d, 1H, J=7), 8.86 (s, 1H).

M.S.: m/e 274 (M$^+$, 100)

Analysis: Calc'd for C$_{17}$H$_{14}$N$_4$.CH$_3$SO$_3$H.1.25H$_2$O: C, 55.02; H, 5.26; N, 14.26%. Found: C, 55.15; H, 5.01; N, 14.13%.

EXAMPLE 28

9-(4-Butoxyanilino)-1H-pyrazolo[3,4-f]quinoline hydrochloride $^1$H NMR: δ 0.94 (t, 3H, J=6), 1.42 (m, 2H), 1.70 (m, 2H), 4.02 (t, 2H, J=5), 6.94 (s, 1H, J=7), 7.10 (d, 1H, J=8), 7.44 (d, 2H, J=8), 7.66 (d, 1H, J=9), 8.32 (d, 1H, J=9), 8.44 (d, 1H, J=7), 8.84 (s, 1H).

M.S.: m/e 332 (M$^+$, 100).

EXAMPLE 29

6-Amino-4-(m-anisidino)quinoline hydrochloride

The title compound was prepared from the corresponding 6-nitro compound by catalytic reduction of the nitro group followed by treatment with HCl in ether. The 6-nitro-4-(m-anisidino)quinoline compound was prepared in an analogous fashion to Example 9 with the modification that 4-nitroaniline was used as the starting material instead of 6-aminoindazole.

$^1$H NMR: δ 3.79 (s, 3H), 6.78 (d, 2H, J=7), 6.9–7.0 (m, H), 7.3–7.5 (m, 2H), 7.70 (s, 1H), 7.92 (d, 1H, J=9).

M.S.: m/e 265 (M+, 100).

EXAMPLE 30

6-Amino-4-(p-butoxyanilino)quinoline hydrochloride

The title compound was prepared from the corresponding -nitro compound by catalytic reduction of the nitro group followed by treatment with HCl in ether. The 6-nitro-4-(p-butoxyanilino) quinoline compound was prepared in an analogous fashion to Example 9 with the modification that 4-nitroaniline was used as the starting material instead of 6-aminoindazole and p-butoxyaniline was used in the displacement of the 4-chloro substituent instead of m-anisidine.

$^1$H NMR: δ 0.96 (t, 3H, J=6), 1.44 (m, 2H), 1.72 (m, 2H), 4.02 (t, 2H, J=6), 6.52 (d, 1H, J=7), 7.08 (d, 2H, J=8), 7.32 (d, 2H, J=8), 7.50 (d, 1H, J=9), 7.72 (s, 1H), 7.88 (d, H, J=8), 8.22 (br s, 1H).

M.S.: m/e 307 (M+, 100).

EXAMPLE 31

6-Amino-4-(3,4-difluoroanilino)-2-phenylquinoline hydrochloride

The title compound was prepared by a procedure similar to that described in Example 12.

$^1$H NMR: δ 6.98 (s, 1H), 7.4–7.8 (m, 8H), 7.90 (d, 2H, J=7), 8.20 (d, 1H, J=9).

M.S.: m/e 347 (M+, 100).

Analysis: Calc'd for $C_{21}H_{15}N_3F_2 \cdot 2HCl$: C, 60.01; H, 4.08; N, 10.00%. Found: C, 60.07; H, 4.21; N, 9.79%.

EXAMPLE 32

4-(p-Cyclohexylmethoxyanilino]-2-phenyl-6-ureidoquinoline hydrochloride

This compound was prepared from the corresponding 6-amino- 4-(p-cyclohexylmethoxyanilino)-2-phenylquinoline with trichloroacetyl isocyante in THF followed by cleavage of the trichloroacetyl group with methanol/sulfuric acid. The hydrochloride salt was formed by treatment with HCl in ether.

$^1$H NMR: δ 1.0–1.3 (m, 5H), 1.6–1.9 (m, 6H), 3.80 (d, H, J=5), 6.28 (br s, 2H), 6.74 (s, 1H), 7.06 (d, 2H, J=8), 7.38 (d, 2H, J=8), 7.6 (m, 3H), 7.78 (m, 2H), 7.96 (d, 1H, J=9), 8.10 (d, 1H, J=9), 8.58 (s, 1H), 9.32 (s, 1H).

M.S.: m/e 466 (M+, 30)

High Resolution Mass Spectrum: Calc'd for $C_{29}H_{30}N_4O_2$: 466.2369. Found: 466.2396.

EXAMPLE 33

6-Acetamido-4-(p-cyclohexylmethoxyanilino)-2-phenylquinoline hydrochloride

This compound was prepared from the corresponding 6-amino- 4-(p-cyclohexylmethoxyanilino)-2-phenylquinoline with acetic anhydride, DMAP, and triethylamine in methylene chloride, followed by treatment with HCl to form the hydrochloric salt.

$^1$H NMR: δ 1.0–1.3 (m, 5H), 1.6–1.9 (m, 6H), 2.18 (s, H), 3.82 (d, 2H, J=6), 6.80 (s, 1H), 7.08 (d, 2H, J=9), 7.42 (d, 2H, J=9), 7.6 (m, 3H), 7.83 (d, 2H, J=7), 7.96 (d, H, J=9), 8.26 (d, 1H, J=9), 8.95 (s, 1H).

M.S.: m/e 465 (M+, 100).

High Resolution Mass Spectrum: Calc'd for $C_{30}H_{31}N_3O_2$: 465.2416. Found: 465.2434.

EXAMPLE 34

$N^4$-[4-(Cyclohexylmethyloxy)phenyl]-2-methylquinolin-4, 8-diamine Hydrochloride Hemihydrate A. N-[4-(Cyclohexylmethyloxy)phenyl]-2-methyl-8-nitroquinolin- 4-amine Hydrochloride Hydrate A solution of 1.0 g (4.5 mmol) of 4-chloro-2-methyl-8-nitroquinoline, 1.0 g (4.9 mmol) of 4-(cyclohexylmethyloxy)aniline and 30 mL of ethanol was heated under reflux for five hours. After cooling to room temperature, the reaction solution was evaporated to a residue which was slurried in in diethyl ether and filtered to furnish 2.0 g (99%) of N-[ 4-(cyclohexylmethyloxy)phenyl]-2-methyl-8-nitroquinolin-4-amine hydrochloride hydrate: m.p. 211°–214° C. (uncorr.).

Anal. Calcd for $C_{23}H_{25}N_3O_3$, HCl, $H_2O$ (445.94): C, 61.94; H, 6.33;N, 9.43. Found: C, 62.24; H, 6.13; N, 9.14.

B. $N^4$-[4-(Cyclohexylmethyloxy)phenyl]-2-methylquinolin-4,8-diamine Hydrochloride Hemihydrate Palladium-on-carbon (180 mg of 5% material) was added to a solution of 100 mL of ethanol and 1.8 g (4.0 mmol) of the nitroquinoline described immediately above. The mixture was then shaken in a Parr apparatus under three atmospheres of hydrogen for an hour. The mixture was filtered, and the filtrate was evaporated under reduced pressure to give 1.0 g (61%) of $N^4$-[4-(cyclohexylmethyloxy)phenyl]-2-methylquinolin- 4,8-diamine hydrochloride hemihydrate: m.p. 274°–277° C. A small portion was recrystallized from acetic acid for analysis; m.p. 280°–284° C.

Anal. Calcd for $C_{23}H_{27}N_3O$, HCl, 0.5 $H_2O$ (406.945): C, 67.88; H, 7.18; N, 10.33. Found: C, 67.91; H, 6.89; N, 10.21.

EXAMPLE 35

4-(4-Butylphenylamino)-2-methylquinolin-6-ol Hydrobromide Hydrate

A. N-(4-Butylphenyl)-6-methoxy-2-methylquinolin-4-amine. In a 100 mL three-neck round bottom flask under a nitrogen atmosphere and with magnetic stirring, a solution of 502 mg (2.42 mmol) of 4-chloro-6-methoxy-2-methylquinoline, 450 mg (3.02 mmol) of 4-butylaniline and 25 mL of ethanol·was heated under reflux for an hour. The reaction solution was evaporated under reduced pressure to furnish a residue which was then chromatographed on silica gel (eluant 9:1 chloroform-methanol) to give 511 mg of the desired product. The sample was recrystallized from ethanol-water to give 320 mg (41%) of pure N-(4-butylphenyl)-6-methoxy-2-methylquinolin- 4-amine: m.p. 200°–201° C.

Anal. Calcd for $C_{21}H_{24}N_2O$ (320.422): C, 78.82;H, 7.56; N, 8.75. Found: C, 78.49; H, 7.45; N, 8.71.

B. 4-(4-Butylphenylamino)-2-methylquinolin-6-ol Hydrobromide Hydrate

Under a nitrogen atmosphere and with magnetic stirring, a solution of 17.5 mL of 48% hydrobromic acid and 142 mg (0.442 mmol) of N-(4-butylphenyl)-6-methoxy-2-methylquinolin- 4-amine was heated under reflux overnight. The reaction mixture was allowed to cool to room temperature whereupon a precipitate formed. The mixture was filtered and washed with ethyl acetate to afford 92 mg of solid material. This was recrystallized from 2-propanol to give 55 mg (31%) of 4-(4-butylphenylamino)-2-methylquinolin-6-ol hydrobromide hydrate.: m.p. 264°–265° C.

Anal. Calcd for $C_{20}H_{22}N_2O$, HBr, $H_2O$ (405.324): C, 59.27; H, 6.22; Br, 19.71; N, 6.91. Found: C, 59.52; H, 6.31; Br, 19.32; N, 6.84.

EXAMPLE 36

4-(4-Chlorophenylamino)-2-methylquinolin-6-ol Hydrobromide Hydrate

A. N-(4-Chlorophenyl)-6-methoxy-2-methylquinolin-4-amine hydrochloride

In a manner similar to that described in Example 35, Part A, 4-chloro-6-methoxy-2-methylquinoline and 4-chloroaniline were transformed into N-(4-chlorophenyl)-6-methoxy- 2-methylquinolin-4-amine hydrochloride: m.p. 305°–307° C.

Anal. Calcd for $C_{17}H_{15}ClN_2O$, HCl (335.225): C, 60.90; H, 4.81; N, 8.36. Found: C, 60.92; H, 4.78; N, 8.33.

B. 4-(4-Chlorophenylamino)-2-methylquinolin-6-ol Hydrobromide Hydrate

In a manner similar to that described in Example 35, Part B, N-(4-chlorophenyl)-6-methoxy-2-methylquinolin-4-amine hydrochloride was transformed into the title compound: m.p. 308°–310° C.

Anal. Calcd for $C_{16}H_{13}ClN_2O$, HBr, $H_2O$ (383.665): C, 50.09; H, 4.20; N, 7.30. Found: C, 49.68; H, 4.09; N, 7.17.

EXAMPLE 37

4-(4-Chlorophenylamino)-2-phenylquinolin-6-ol Hydrobromide Dihydrate

A. N-(4-chlorophenyl)-6-methoxy-2-phenylquinolin-4-amine Hydrochloride Hydrate

In a manner similar to that described in Example 35, part A, 4-chloro-6-methoxy-2-phenylquinoline and 4-chloroaniline were transformed into 1.2 g (80%) of the title compound: m.p.>250° C.

Anal. Calcd for $C_{22}H_{17}ClN_2O$, HCl, $H_2O$ (415.306): C, 63.62; H, 4.85; N, 6.75. Found: C, 63.68; H, 4.86; N, 6.77.

B. 4-(4-Chlorophenylamino)-2-phenylquinolin-6-ol Hydrobromide Dihydrate

In a manner similar to that described in Example 35, Part B, N-(4-chlorophenyl)-6-methoxy-2-phenylquinolin-4-amine hydrochloride hydrate was transformed into the title compound: m.p. 180°–185° C. (decomp.).

Anal. Calcd for $C_{21}H_{15}ClN_2O$, HBr, $2H_2O$ (463.747): C,54.39; H, 4.35; N, 6.04. Found: C, 54.14; H, 3.82; N, 5.91.

EXAMPLE 38

2-Methyl-4-octylaminoquinolin-6-ol Hydrobromide Hemihydrate

In a 100 mL three-neck round bottom flask under a nitrogen atmosphere and with magnetic stirring, a solution of 1.0 g (4.8 mmol) of 4-chloro-6-methoxy-2-methylquinoline and 10 mL of n-octylamine was heated under reflux for three hours. Upon cooling to room temperature, the reaction mixture formed a glassy solid which was filtered. This was triturated under isopropyl ether filtered and washed with additional ether. The solid was stirred with a mixture of water and ethyl acetate; insolubles were filtered and discarded; the ethyl acetate layer eventually furnished 500 mg of 6-methoxy-2-methyl-N-octylquinolin-4-amine hydrochloride: m.p. 178°–179° C. Without further purification, a solution of 350 mg (1.04 mmol) of this material and 42 mL of 48% hydrobromic acid was heated reflux for 18 hours. Upon cooling, the reaction solution gave a precipitate which was filtered. The filtrate was evaporated to furnish a solid residue. The combined solids were recrystallized from hot water to give 45 mg (12%) of 2-methyl- 4-octylaminoquinolin-6-ol hydrobromide hemihydrate: m.p. 176°–178° C.

Anal. Calcd for $C_{18}H_{26}N_2O$, HBr, 0.5 $H_2O$ (376.328): C, 57.44; H, 7.50; N, 7.45. Found: C, 57.23; H, 7.40; N, 7.23.

EXAMPLE 39

4-[4-(Cyclohexylmethyloxy)phenylamino]-2-methylquinolin- 6-ol Hydrochloride Hydrate A. 4-Chloro-2-methylquinolin-6-ol Under a nitrogen atmosphere in a 500 single-neck round bottom flask equipped with a condenser and a magnetic stirrer, a solution of 2.00 g (9.62 mmol) of 4-chloro-6-methoxy- 2-methylquinoline and 150 mL of 48% hydrobromic acid was heated under reflux for 90 minutes. Upon cooling to room temperature, the reaction solution was evaporated under reduced pressure to afford a solid residue. The residue was slurried in chloroform filtered and washed with chloroform. The solid was next slurried in a mixture of saturated aqueous sodium carbonate and ethyl acetate for 15 minutes, filtered and washed successively with saturated aqueous sodium carbonate, water and ethyl acetate. After air drying there was obtained 741 mg (40%) of 4-chloro-2-methylquinolin- 6-ol: m.p. 233° C.

Anal. Calcd for $C_{10}H_8ClNO$ (193.627): C, 62.03; H, 4.16; N, 7.24. Found: C, 62.02; H, 4.07; N, 7.20.

B. 4-[4-(Cyclohexylmethylox)phenylamino]-2methylquinolin- 6-ol Hydrochloride Hydrate Under a nitrogen atmosphere in a 100 mL three-neck round bottom flask equipped with a magnetic stirrer and condenser, a solution of 580 mg (3.0 mmol) of 4-chloro-2-methylquinolin- 6-ol, 707 mg (3.45 mmol) of 4-(cyclohexylmethyloxy)aniline and 35 mL of ethanol was heated under reflux for three hours. Upon cooling to room temperature a precipitate formed. This was filtered, washed with ethanol, and allowed to dry. There was obtained 1.0 g of a solid that was recrystallized from n-butanol to furnish 811 mg (65%) of the title compound as yellow crystals: m.p. 318°–322° C. (uncorr.).

Anal. Calcd for $C_{23}H_{26}N_2O_2$, HCl, $H_2O$ (416.935): C, 66.25; H, 7.01; N, 6.72. Found: C, 66.18; H, 6.74; N, 6.75.

EXAMPLE 40

4-(3-Methoxyphenylamino)-2-methylquinolin-6-ol Hydrochloride

In a manner similar to that described in Example 39, Part B, 4-chloro-2-methylquinolin-6-ol and m-anisidine were converted into the title compound: m.p. 309°–311° C.

Anal. Calcd for $C_{17}H_{16}N_2O_2$, HCl (316.779): C, 64.45; H, 5.41; N, 8.85. Found: C, 64.15; H, 5.54; N, 8.70.

EXAMPLE 41

4-Hexylamino-2-methylquinolin-6-ol Hydrochloride Hemihemihydrate

In a manner similar to that described in Example 39, Part B, 4-chloro-2-methylquinolin-6-ol and hexylamine were transformed into the title compound: m.p. 234°–236° C.

EXAMPLE 42

4-Dodecylamino-2-methylquinolin-6-ol Hydrochloride Hydrate

In a manner similar to that described in Example 39, Part B, 4-chloro-2-methylquinolin-6-ol and dodecylamine were transformed into the title compound: m.p. 198°–203° C.

Anal. Calcd for $C_{22}H_{34}N_2O$, HCl, $H_2O$ (396.989): C, 66.56; H, 9.39; N, 7.06. Found: C, 66.05; H, 9.41; N, 6.98.

EXAMPLE 43

4-Dodecylamino-2-methylquinolin-6-ol Methanesulfonate

A stirred mixture of 1.2 g (3.0 mmol) of the hydrochloride salt described in Example 42, ethyl acetate and water was adjusted to pH 8 by the addition of aqueous 4 N sodium hydroxide. The organic phase was evaporated under reduced pressure to afford 1.0 g (2.9 mmol) of the free base as a yellow solid. This was treated with an equivalent of methanesulfonic acid. The resulting solid was triturated with isopropyl ether and then recrystallized from acetonitrile to furnish 600 mg of the title product as golden needles: m.p. 123°–125° C.

Anal. Calcd for $C_{22}H_{34}N_2O$, $CH_3SO_3H$ (438.62): C, 62.98; H, 8.73; N, 6.38. Found: C, 63.05; H, 8.73; N, 6.46.

EXAMPLE 44

4-Decylamino-2-methylquinolin-6-ol Methanesulfonate

In the manner similar to those described in Example 39, Part B, and Example 43, 4-chloro-2-methylquinolin-6-ol and decylamine (neat at 130° C.) were transformed into the title compound: m.p. 100°–102° C.

Anal. Calcd for $C_{20}H_{30}N_2O$, $CH_3SO_3H$ (410.57): C, 61.43; H, 8.34; N, 6.82. Found: C, 61.36; H, 8.39; N, 6.73.

EXAMPLE 45

4-Tetradecyl-2-methylquinolin-6-ol Hydrochloride Hydrate

A solution of 150 mg (0.78 mmol) of 4-chloro-2-methylquinolin-6-ol, 174 mg (0.81 mmol) of n-tetradecylamine, and 5 mL of n-butanol was heated under reflux for 24 hours. Excess butanol was removed by codistillation with cyclohexane. The residue was chromatographed on 30 g of silica gel (eluent 1:9 methanol-dichloromethane) to furnish crude product. This was taken up in methanol, and the solution was treated with dry hydrogen chloride gas. The solution was evaporated under reduced pressure to give the title compound as crystalline material: m.p. 180°–183° C.

Anal. Calcd for $C_{24}H_{38}N_2O$, HCl, $H_2O$ (425.04): C, 67.82; H, 9.72; N, 6.59. Found: C, 67.73; H, 9.35; N, 6.64.

EXAMPLE 46

4-[(3-Methoxyphenyl)amino]quinolin-6-ol Mixed Hydrobromide and Hydrochloride Salts A. 4-Chloroquinolin-6-ol Hydrobromide In a flame dried three-neck 50 mL round bottom flask equipped with a rubber septum and a mechanical stirrer, and under a nitrogen atmosphere at room temperature, 4.0 mL of 1.0M boron tribromide in dichloromethane (Aldrich Chemical Co.) was added portionwise through gas tight syringe to a solution of 727 mg (3.75 mmol) of 4-chloro-8-methoxyquinoline and 5.0 mL of dichloromethane. A thick solid formed immediately and after 0.5 hour of stirring another 4.0 mL portion of boron tribromide solution was added and stirring was continued overnight. The reaction mixture was treated dropwise with methanol. The solution was evaporated under reduced pressure, and the residue titurated with dichloromethane and filtered to afford 844 mg (86%) of the title compound: m.p. 243°–244° C.

Anal. Calcd for $C_9H_6ClNO$, HBr (260.51): C, 41.49; H, 2.71; N, 5.38. Found: C, 41.46; H, 2.63; N, 5.27.

B. 4-[(3-Methoxyphenyl)amino]quinolin-6-ol Mixed Hydrobromide and Hydrochloride Salts A solution of 245 mg (0.94 mmol) of 4-chloroquinolin-6ol hydrobromide, 0.3 mL (2.72 mmol) of m-anisidine and 30 mL of ethanol was heated under reflux for an hour. The reaction solution was evaporated under reduced pressure to afford a solid residue which was then slurried first in diethyl ether and then in acetone. The solid was recrystallized from hot acetone to give 200 mg (65%) of the title product: m.p. 241°–243° C.

Anal. Calcd for $C_{16}H_{14}N_2O_2$, 0.6 HBr, 0.4 HCl (329.42): C, 58.33; H, 4.59; Br, 14.55; Cl, 4.30; N, 8.51. Found: C, 57.68; H, 4.52; Br, 14.17; Cl, 4.37;. N, 8.30.

EXAMPLE 47

4-[(4-Cyclohexylmethyloxy)phenylamino]quinolin-6-ol Mixed Hydrobromide and Hydrochloride Salts In a manner similar to that described in Example 46, Part B, 4-chloroquinolin-6-ol hydrobromide and 4-(cyclohexylmethyloxy)aniline were transformed into 267 mg (67%) of the title compound: m.p. 235°–238° C.

Anal. Calcd for $C_{22}H_{24}N_2O_2$, 0.9 HBr, 0.1 HCl (424.90): C, 62.18; H, 5.93; N, 6.59. Found: C, 62.23; H, 6.32; N, 6.56.

EXAMPLE 48

4-(Cyclohexylamino)quinolin-6-ol Hydrobromide Hydrate 4-(Cyclohexylamino)quinolin-6-ol Hydrobromide Hydrate. A solution of 245 mg (0.94 mmol) of 4-chloroquinolin-6-ol hydrobromide and 1.0 mL of cyclohexylamine was heated under reflux overnight. Excess volatile components of the reaction mixture were evaporated under reduced pressure. The residue was slurried with isopropyl ether and then filtered. The solids were recrystallized from hot acetic acid to afford 129 mg (40%) of the title compound: m.p. 280°–285° C. (dec.).

Anal. Calcd for $C_{15}H_{15}N_2O_2$, HBr, $H_2O$ (341.24): C, 52.79; H, 6.20; N, 7.68. Found: C, 52.85; H, 6.33; N, 8.12.

EXAMPLE 49

4-(Dodecylamino)quinolin-6-ol Methanesulfonate

A. 4-Chloroquinolin-6-ol

A solution of 4.99 g (18.1 mmol) of 4-chloro-6-methoxyquinoline and 50 mL of 48% hydrobromic acid is heated under reflux for seven hours. Upon cooling to room temperature, the reaction solution afforded a dark solid that was then slurried in water. The aqueous mixture was adjusted to pH 10 by the addition of 4N sodium hydroxide. The resulting solid was filtered, washed with water and air-dried to give 1.83 g (56%) of 4-chloroquinolin-6-ol: m.p. 223° C.

B. 4-(Dodecylamino)quinolin-6-ol Methanesulfonate

A mixture of 800 mg (4.4 mmol) of 4-chloroquinolin-6-ol and 4.12 g (22.2 mmol) of dodecylamine was heated at 130° C. for nine hours. Upon cooling to room temperature the dark reaction mixture was slurried with isopropyl ether and then filtered. The solids were boiled with water, filtered, and then air dried to give 441 mg (30%) of the waxy free base. A solution of the free base, 92 μL of methanesulfonic acid, and methanol afforded 550 mg (29%) of the title compound as crystals: m.p. 148°–149° C.

Anal. Calcd for $C_{21}H_{32}N_2O$, $CH_3SO_3H$ (424.59): C, 62.23; H, 8.48; N, 6.59. Found: C, 62.23; H, 8.55; N, 6.63.

EXAMPLE 50

4-(Decylamino)quinolin-6-ol Hydrochloride

In a manner similar to that described in Example 49, Part B, 4-chloroquinolin-6-ol and decylamine were transformed into the title compound as the hydrochloride salt: m.p. 197°–199° C.

Anal. Calcd for $C_{19}H_{28}N_2O$, HCl, (336.89): C, 67.74; H, 8.67; N, 8.31. Found: C, 67.93; H, 8.92; N, 8.16.

EXAMPLE 51

4-(4-Butylphenylamino)-2-methylquinolin-7-ol Hydrobromide Hemihydrate

A. N-(4-Butylphenyl)-7-methoxy-2-methylquinolin-4-amine Hydrochloride

In a manner similar to that described in Example 35, Part A, 4-chloro-7-methoxy-2-methylquinoline and 4-butylaniline were transformed into the title compound: m.p. 245°–246° C.

Anal. Calcd for $C_{21}H_{24}N_2O$, HCl (356.883): C, 70.67; H, 7.06; N, 7.85. Found: C, 70.51; H, 6.93; N, 7.81.

B. 4-(4-Butylphenylamino)-2-methylquinolin-7-ol Hydrobromide Hemihydrate

In a manner similar to that described in Example 35, Part B, N-(4-butylphenyl)-7-methoxy-2-methylquinolin-4-amine Hydrochloride was transformed into the title compound: m.p. 328°–330° C.

Anal. Calcd for $C_{20}H_{22}N_2O$, HBr, 0.5 $H_2O$ (396.316): C, 60.92; H, 6.10; N, 7.07. Found: C, 60.92; H, 5.63; N, 7.04.

EXAMPLE 52

4-[4-(Cyclohexylmethyloxy)phenylamino]-2-methylquinolin-7-ol Mixed Hydrobromide and Hydrochloride Salts A. 4-Chloro-2-methylquinolin-7-ol Hydrobromide In a manner similar to that described in Example 46, Part A, 4-chloro-7-methoxy-2-methylquinoline was tranformed into the title product: m.p.>300° C.

Anal. Calcd for $C_{10}C_1NO$, HBr (274.54): C, 43.75; H, 3.30; N, 5.10. Found: C, 44.15; H, 3.21; N, 4.98.

B. 4-Chloro-2-methylquinolin-7-ol

A mixture of 2.33 g (8.49 mmol) of the hydrobromide salt described above, ethyl acetate and aqueous saturated sodium carbonate was stirred for an hour. The organic phase was then washed with aqueous saturated NaCl, dried over anhydrous magnesium sulfate, filtered, and evaporated to furnish 1.6 g (100%) of 4-chloro-2-methylquinolin-7-ol.

C. 4-[4-(Cyclohexylmethyloxy)phenylamino]-2-methylquinolin- 7-ol Mixed Hydrobromide and Hydrochloride Salts In a manner similar to that described in Example 46, Part B, 4-chloro-2-methylquinolin-7-ol hydrobromide and 4-(cyclohexylmethyloxy)aniline were tranformed into the title compound: m.p. 330°–333° C.

Anal. Calcd for $C_{23}H_{26}N_2O_2$, 0.5 HBr, 0.5 HCl (421.14): C, 65.59; H, 6.46; N, 6.65. Found: C, 65.51; H, 6.26; N, 6.55.

EXAMPLE 53

4-(Dodecylamino)-2-methylquinolin-7-ol Methanesulfonate

In a manner similar to that described in Example 49, Part B, 4-chloro-2-methylquinolin-7-ol and dodecylamine were transformed into the title compound: m.p. 186°–187° C.

Anal. Calcd for $C_{22}H_{34}N_2O$, $CH_3SO_3H$ (438.62): C, 62.98; H, 8.73; N, 6.38. Found: C, 62.90; H, 8.55; N, 6.34.

EXAMPLE 54

4-(Decylamino)-2-methylquinolin-7-ol Methanesulfonate

In a manner similar to that described in Example 49, Part B, 4-chloro-2-methylquinolin-7-ol and decylamine were transformed into the title compound: m.p. 188°–189° C.

Anal. Calcd for $C_{20}H_{30}N_2O$, $CH_3SO_3H$ (410.57): C, 61.43; H, 8.34; N, 6.82. Found: C, 61.53; H, 8.51; N, 6.75.

EXAMPLE 55

4-(4-Butylphenylamino)quinolin-8-ol Hydrochloride Hydrate

A. N-(4-Butylphenyl)-8-methoxyquinolin-4-amine Hydrochloride Hydrate

In a manner similar to that described in Example 35, Part A, 4-chloro-8-methoxyquinoline and 4-butylaniline were tranformed into the title compound: m.p. 132°–134° C.

Anal. Calcd for $C_{20}H_{22}N_2O$, HCl, $H_2O$ (360.87): C, 66.56; H, 6.98; N, 7.76. Found: C, 66.16; H, 6.85; N, 7.82.

B. 4-(4-Butylphenylamino)quinolin-8-ol Hydrochloride Hydrate

In a flame dried single-neck round bottom flask equipped with a Dean-Stark trap and a condenser, a solution of 1.0 g (2.9 mmol) of N-(4-butylphenyl)-8-methoxyquinolin-4-amine hydrochloride and 20 mL of toluene was treated with 1.9 g (14.5 mmol) of anhydrous aluminum chloride. This was heated under reflux for five hours, and then allowed to cool to room temperature. The reaction solution was treated dropwise with water until a sticky solid formed. Work-up of the mixture eventually afforded mg of crude product. This was recrystallized from water-formic acid to furnish 340 mg (34%) of the title compound: m.p. 269° C.

Anal. Calcd for $C_{19}H_{20}N_2O$, HCl, $H_2O$ (346,847): C, 65.79; H, 6.68; N, 8.07. Found: C, 65.34; H, 6.29; N, 7.84.

EXAMPLE 56

4-[4-(Cyclohexylmethyloxy)phenylamino]quinolin-8-ol Hydrochloride Hydrate

A. 4-Chloroquinolin-8-ol Hydrobromide

In a manner similar to that described in Example 46, Part A, 4-chloro-8-methoxyquinoline was tranformed into the title product: m.p. 232°–233° C.

B. 4-Chloro-quinolin-8-ol

A solution of 1.3 g of the hydrobromide salt and 50 mL of water was adjusted to pH 9 by the addition of 4N sodium hydroxide. The resulting precipitate was filtered, washed with water, and air-dried to give 790 mg (52%) of the title compound: m.p. 143°–145° C.

C. 4-[4-(cyclohexylmethyloxy)phenylamino]quinolin-8-ol Hydrochloride Hydrate

In a manner similar to that described in Example 46, Part B, 4-chloro-quinolin-8-ol hydrobromide and 4-(cyclohexylmethyloxy)aniline were tranformed into and the title product: m.p. 286°–288° C. (from methanol-acetonitrile).

Anal. Calcd for $C_{22}H_{24}N_2$, HCl, $H_2O$ (402.89): C, 65.58; H, 6.75; N, 6.95. Found: C, 65.82; H, 6.19; N, 6.90.

EXAMPLE 57

4-(Dodecylamino)quinolin-8-ol Hydrochloride

In a manner similar to that described in Example 49, Part B, 4-chloroquinolin-8-ol and n-dodecylamine were transformed into the title compound: m.p. 189°–190° C.; m/e 328 (molecular ion); NMR spectum consistent with assigned structure.

EXAMPLE 58

4-[4-(Cyclohexylmethyloxy)phenylamino]quinolin-6,8-diol Hydrochloride

A. 6,8-Dimethoxyquinolin-4-ol

In a three neck round-bottom flask equipped with a reflux condenser and a mechanical stirrer, a solution of 10.0 g (69.3 mmol) of 2,2-dimethyl-1,3-dioxan-4,6-dione (Meldrum's acid) and 46 mL (277 mmol) of triethyl orthoformate was treated with 11.1 g (72.7 mmol) of 2,4-dimethoxyaniline. The mixture was heated at 85° C. for two hours. Upon cooling to room temperature, the reaction mixture was diluted with isopropyl ether and filtered to furnish 18.7 g of 5-[(2,4-dimethoxyphenyl)aminomethylene] 2,2-dimethyl-1,3-dioxan-4,6-dione as a bright orange solid. This solid was then added portionwise to 80 mL of a boiling solution of biphenyl and diphenyl ether/biphenyl, (Dowtherm, trademark). After the final addition heating was continued for just 5 minutes. After cooling to room temperature, the reaction mixture was stored in the refrigerator overnight, and then stirred with isopropyl ether for an hour. The solids were filtered and washed with isopropyl ether to afford 11.8 g (83%) of 6,8-dimethoxyquinolin-4-ol: m.p. 221°–224° C.

B. 4-Chloro-6,8-dimethoxyquinoline

A solution of 6.5 g (31.6 mmol) of 6,8-dimethoxyquinolin-4-ol, 29 mL (316 mmol) of phosphorous oxychloride and 2.6 mL of N,N-dimethylformamide was stirred at room temperature for seven hours. The reaction solution was poured into a stirred mixture of ice and water. The aqueous mixture was washed three times with 300 mL portions of ethyl acetate, and then adjusted to pH 6 by the addition of solid sodium carbonate. 4-Chloro-6,8-dimethoxyquinoline was thus obtained as a colorless solid: yield 5.73 g (81%). The product was recrystallized from hot water for analysis: m.p. 115°–116° C.

Anal. Calcd for $C_{11}H_{10}ClNO_2$ (223.66): C, 59.07; H, 4.50; N, 6.26. Found: C, 58.98; H, 4.24; N, 6.18.

C. 4-Chloroquinolin-6,8-diol Hemihydrate

In a manner similar to that described in Example 46, Part A, 4-chloro-6,8-dimethoxyquinoline was tranformed into 4-chloroquinolin-6,8-diol hemihydrate: m.p. 209°–211° C.

Anal. Calcd for $C_9H_6C_1NO_2$, 0.5 H2O (204.61): C, 52.83; H, 3.44; N, 6.84. Found: C, 52.95; H, 2.90; N, 6.81.

D. 4-[4-(Cyclohexylmethyloxy)phenylamino]quinolin-6,8-diol Hydrochloride

In a manner similar to that described in Example 39, Part B, 4-chloroquinolin-6,8-diol hemihydrate and 4-(cyclohexylmethyloxy)aniline were tranformed into the title compound: m.p. 294° C. (dec.).

Anal. Calcd for $C_{22}H_{24}N_2O_3$, HCl (400.89): C, 65.91; H, 6.25; N, 6.98. Found: C, 65.63; H, 6.02; N, 7.05.

EXAMPLE 59

4-[4-(Cyclohexylmethyloxy)phenylamino]quinolin-6-methanol Methanesulfonate

A. Ethyl 4-Hydroxyquinoline-6-carboxylate

In a manner similar to that described in Example 58, Part A., 10 g (69 mmol) of 2,2-dimethyl-1,3-dioxan-4,6-dione and 11.4 g (69 mmol) of ethyl 4-aminobenzoate were tranformed into the title product: yield 10.86 g (72%); m.p. 233°–234° C.

Anal. Calcd for $C_{12}H_{11}NO_3$ (217.22): C, 66.35; H, 5.10; N, 6.45. Found: C, 66.04; H, 4.92; N, 6.39.

B. Ethyl 4-Chloroquinoline-6-carboxylate

In a manner similar to that described in Example 58, Part B., 7.34 g (33.7 mmol) of ethyl 4-hydroxyquinolin-6-carboxylate was transformed into the title compound: yield 4.9 g (62%); m.p. 84°–85° C.

Anal. Calcd for $C_{12}H_{10}ClNO_2$ (235.66): C, 61.16; H, 4.27; N, 5.94. Found: C, 61.35; H, 4.28; N, 5.82.

C. Ethyl 4-[4-(cyclohexylmethyloxy)phenylamino]quinolin-6-carboxylate Hydrochloride In a manner similar to that described in Example 39, Part B., 2.0 g (8.48 mmol) of ethyl 4-chloroquinolin-6-carboxylate and 1.74 g (8.48 mmol) of 4-(cyclohexylmethyloxy)aniline were transformed into the title compound: yield 3.41 g (92%); m.p. 251°–253° C.

Anal. Calcd for $C_{25}H_{28}N_2O_3$, HCl (440.96): C, 68.09; H, 6.62; N, 6.35. Found: C, 68.00; H, 6.40; N, 6.07.

D. 4-[4-(Cyclohexylmethyloxy)phenylamino]quinolin-6-methanol Methanesulfonate

A suspension of 519 mg (1.18 mmol) of the compound described in Part C, above, in water was adjusted to pH 12 by the addition 4N sodium hydroxide, and stirred for 30 minutes. The aqueous mixture was then extracted three times with 250 mL portions of dichloromethane. The combined extracts were washed with saturated aqueous sodium chloride, and dried over anhydrous sodium sulfate. The organic phase was filtered and evaporated under reduced pressure. The residue was dried in a vacuum oven for 72 hours, and then slurried with magnetic stirring in 7 mL of dichloromethane. At room temperature, 1.5 mL of 1.0M borane-methylsulfide in dichloromethane (Aldrich) was added to the slurry. The reaction mixture was then heated under reflux for four hours, and then allowed to cool. Methanol was added dropwise to the reaction mixture, and stirring was continued for an hour. Volatile components were evaporated from the reaction mixture, and the residue was chromatographed on 50 g of silica gel (eluent: 5:95 methanol-dichloromethane) to furnish crude 4-[4-(cyclohexylmethyloxy)phenylamino] quinolin-6-methanol. An additional chromatography procedure gave 40 mg of pure free base. To a methanol solution of the free base was added 10 μL of methanesulfonic acid. Removal of the methanol led to a yellow oil which was then crystallized from 2-propanol and isopropyl ether to give the tile compound: yield 15 mg (3%); m.p. 158°–160° C.; m/e 362; NMR (deuterochloroform) showed a new peak at δ 4.69 ppm (s, 2H, CH$_2$OH), and no peaks indicating the presence of an ethoxy group.

We claim:

1. A compound of the formula

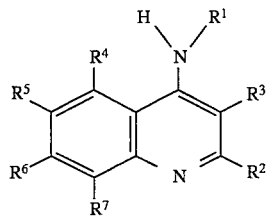

wherein $R^1$ is ($C_3$–$C_{18}$) alkyl, ($C_3$–$C_{12}$) cycloalkyl or phenyl optionally substituted with from one to three substituents independently selected from ($C_1$–$C_6$) alkyl, ($C_1$–$C_6$) alkoxy, halo, cyano, ($C_3$–$C_8$) cycloalkyl-($C_1$–$C_6$)alkoxy wherein the cycloalkyl moiety may be substituted with from one to three ($C_1$–$C_6$)alkyl groups; hydroxyl, benzyloxy, carboxyl, hydroxy-($C_1$–$C_6$) alkyl, pyrrolidino, piperidino, morpholino and —CONHQCOOH wherein Q is ($C_1$–$C_4$) alkylene;

$R^2$ is hydrogen, ($C_1$–$C_6$) alkyl, ($C_3$–$C_7$) cycloalkyl, phenyl or phenyl-($C_1$–$C_6$) alkyl, wherein the phenyl moieties of said phenyl and said phenyl-($C_1$–$C_6$) alkyl may be optionally substituted with from one to three substituents independently selected from ($C_1$–$C_6$) alkyl, ($C_1$–$C_6$)-alkoxy, halo, cyano and benzyloxy;

$R^3$ is hydrogen;

$R^4$ and $R^5$, together with the carbons to which they are attached, form a group of the formula

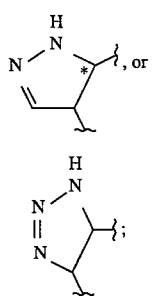

wherein the carbon of group A labelled with an asterisk (*) represents the point of attachment of $R^4$ to the quinoline nucleus and the carbon of group A adjacent to it represents the point of attachment of $R^5$ to the quinoline nucleus;

$R^6$ is hydrogen, hydroxyl, amino, guanidino, —NHC(=NR$^8$)R$^9$, —NHCOR$^{13}$, —NHSO$_2$R$^{13}$ or ureido;

$R^7$ is hydrogen, halo, hydroxyl, amino, —NHC(=NR$^8$)R$^9$, —NHSO$_2$R$^{14}$, —NHCOR$^{14}$, ureido or guanidino;

$R^8$ and $R^9$ are independently selected from hydrogen, phenyl and ($C_1$–$C_6$) alkyl;

$R^{13}$ and $R^{14}$ are independently selected from ($C_1$–$C_6$) alkyl and phenyl optionally substituted with halo, ($C_1$–$C_6$) alkyl or ($C_1$–$C_6$) alkoxy;

except for 9-(p-anisidino)-2-methyl-1H-pyrazolo[3,4-f] quinoline hydrochloride, 9-(cyclohexylamino)-1H-pyrazolo[ 3,4-f]quinoline methanesulfonate, 9-(cyclopentylamino)- 1H-pyrazolo[3,4-f]quinoline methanesulfonate or a pharmaceutically acceptable salt thereof.

2. A compound according to claim 1, wherein $R^3$, $R^6$ and $R^7$ are hydrogen and $R^4$ and $R^5$, together with the carbons to which they are attached, form a group of the formula

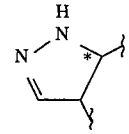

wherein the carbon of group A labelled with an asterisk (*) represents the point of attachment of $R^4$ to the quinoline nucleus and the carbon of group A adjacent to it represents the point of attachment of $R^5$ to the quinoline nucleus.

3. A compound according to claim 1 wherein $R^3$, $R^6$ and $R^7$ are hydrogen.

4. A compound according to claim 1, wherein said compound is selected from the group consisting of:

9-(m-Anisidino)-7-methyl-1H-pyrazolo[3,4-f]quinoline;

9-(p-Cyclohexylmethoxyanilino)-7-methyl-1H-pyrazolo [3,4-f] quinoline;

9-(Cyclohexylamino)-7-methyl-1H-pyrazolo[3,4-f] quinoline hydrochloride; and 9-(p-Cyclohexylmethoxyanilino)-1H-pyrazolo[3,4-f] quinoline.

5. A pharmaceutical composition comprising an amount of a compound according to claim 1 effective in stimulating or enhancing the immune response of a vertebrate, and a pharmaceutically acceptable carrier.

6. A method of stimulating or enhancing the immune response of a vertebrate, comprising administering to said vertebrate an immune response stimulating or enhancing amount of a compound according to claim 1.

* * * * *